(12) United States Patent
Kendall et al.

(10) Patent No.: US 7,071,159 B2
(45) Date of Patent: Jul. 4, 2006

(54) INHIBITOR OF VASCULAR ENDOTHELIAL CELL GROWTH FACTOR

(75) Inventors: Richard L. Kendall, Edison, NJ (US); Kenneth A. Thomas, Jr., Chatham Borough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 645 days.

(21) Appl. No.: 10/101,018

(22) Filed: Mar. 19, 2002

(65) Prior Publication Data

US 2003/0120038 A1     Jun. 26, 2003

Related U.S. Application Data

(60) Division of application No. 09/232,773, filed on Jan. 15, 1999, now abandoned, which is a division of application No. 08/786,164, filed on Jan. 21, 1997, now Pat. No. 5,861,484, which is a division of application No. 08/232,538, filed on Apr. 21, 1994, now Pat. No. 5,712,380, which is a continuation-in-part of application No. 08/038,769, filed on Mar. 25, 1993, now abandoned.

(51) Int. Cl.
*A61K 38/18* (2006.01)
*C07K 14/00* (2006.01)
*G01N 33/566* (2006.01)

(52) U.S. Cl. ............... 514/2; 530/300; 530/350; 435/375; 435/7.21

(58) Field of Classification Search ............ 514/2; 530/300, 350; 435/375, 7.21
See application file for complete search history.

(56) References Cited

FOREIGN PATENT DOCUMENTS

| WO | WO 92/14748 | 9/1992 |
|---|---|---|
| WO | WO 94/10202 | 5/1994 |
| WO | WO 94/11499 | 5/1994 |

OTHER PUBLICATIONS

Conn, G. et al. "Amino acid and cDNA sequences of a vascular endothelial cell mitogen that is homologous to platelet-derived growth factor", Proc., Natl. Acad. Sci. USA, 1990, vol. 87, pp. 2628-2632.

Ferrara, N. & Henzel W. "Pituitary Follicular Cells Secrete a Novel Heparin-Binding Growth Factor Specific for Vascular Endothelial Cells", Biochem. and Biophys. Res. Comm., 1989, vol. 161, pp. 851-858.

Gospodarowicz, D. et al. "Isolation and characterization of a vascular endothelial cell mitogen produced by pituitary-derived folliculo stellate cells", Proc. Natl. Acad. Sci. USA, 1989, vol. 86, pp. 7311-7315.

Pamela J. Keck et al. "Vascular Permeability Factor, an Endothelial Cell Mitogen Related to PDGF", Science, 1989, vol. 246, pp. 1309-1312.

De Vries, C. et al. "The *fms*-Like Tyrosine Kinase, a Receptor for Vascular Enothelial Growth Factor", Science, 1992, vol. 255, pp. 989-991.

Terman, B. et al. "Identification of a new endothelial cell growth factor receptor tyrosin kinase", Oncogene, 1991, vol. 6, 1677-1683.

Terman, B. et al. "Identification of the KDR Tyrosine Kinase as a Receptor for Vascular Endothelial Cell Growth Factor", Biochem. and Biophys. Res. Comm., 1992, vol. 187, pp. 1579-1586.

Shibuya, M. et al. "Nucleotide sequence and expression of a novel human receptor-type tyrosine kinase gene (*flt*) closely related to the *fms* family", Oncogene, 1990, vol. 5, pp. 519-524.

Duan, D. et al. "A Functional Soluble Extracellular Region of the Platelet-derived Growth Factor (PDGF) *B*-Receptor Antagonizes PDGF-stimulated Responses", The J. of Biol. Chem., 1991, vol. 266, pp. 413-418.

(Continued)

*Primary Examiner*—Joseph Murphy
*Assistant Examiner*—Nirmal S. Basi
(74) *Attorney, Agent, or Firm*—J. Mark Hand; Jack L. Tribble

(57) ABSTRACT

The vascular endothelial cell growth factor (VEGF) inhibitors of the present invention are naturally occurring or recombinantly engineered soluble forms with or without a C-terminal transmembrane region of the receptor for VEGF, a very selective growth factor for endothelial cells. The soluble forms of the receptors will bind the growth factor with high affinity but do not result in signal transduction. These soluble forms of the receptor bind VEGF and inhibit its function.

4 Claims, 17 Drawing Sheets

OTHER PUBLICATIONS

Hoshi, H. & McKeehan W. "Brain- and liver cell-derived factors are required for growth of human endothelial cells in serum-free culture", Proc. Natl. Acad. Sci. USA, 1984, vol. 81, pp. 6413-6417.

Sanger, F. et al. "DNA sequencing with chain-terminating inhibitors", Proc. Natl. Acad. Sci. USA, 1977, vol. 74, pp. 5463-5467.

Feinberg A. & Vogelstein B. "A Technique for Radiolabeling DNA Restriction Endonuclease Fragments to High Specific Activity", Anal. Biochem., 1983, vol. 132, pp. 6-13.

Hunter W. & Greenwood F. "Preparation of Iodine-131 Labelled Human Growth Hormone of High Specific Activity", Nature, 1962, vol. 194, pp. 495-496.

Scatchard, G. "The Attractions of Proteins for Small Molecules and Ions", Annals NY Acad. of Sci., 1949, vol. 51, pp. 660-672.

Bikfalvi, A. et al. "Interaction of Vasculotropin/Vascular Endothelial Cell Growth Factor with Human Umbilical Vein Endothelial Cells: Binding, Internalization, Degradation, and Biological Effects", J. of Cell. Phys., 1991, vol. 149, pp. 50-59.

Olsson, I. et al. "The receptors for Regulatory Molecules of Hematopoiesis", Eur. J. Haematol, 1992, vol. 48, pp. 1-9.

Kim, K. et al. "The Vascular Endothelial Growth Factor Proteins: Identification of Biologically Relevant Regions by Neutralizing Monoclonal Antibodies", Growth Factors, 1992, vol. 7, pp. 53-64.

Ueno, H. et al. "Inhibition of PDGF B Receptor Signal Transduction by Coexpression of a Truncated Receptor", Science, 1991, vol. 252, pp. 844-848.

Maliszewski, C. et al. "Cytokine Receptors and B Cell Functions I. Recombinant Soluble Receptors Specifically Inhibit IL-1- and IL-4-Induced B Cell Activities in Vitro", J. of Immunology, 1990, vol. 144, pp. 3028-3033.

Kendall, R. & Thomas, K. "Inhibition of vascular endothelial cell growth factor activity by an endogenously encoded soluble receptor", Proc. Natl. Acad. Sci. USA, vol. 90, pp. 10705-10709.

Millauer, B. et al. "Glioblastoma growth inhibited in vivo by a dominant-negative Flk-1 mutant", Nature, 1994, vol. 367, pp. 576-579.

Millauer, B. et al. "High Affinity VEGF Binding and Developmental Expression Suggest Flk-1 as a Major Regulator of Vasculogenesis and Angiogenesis", Cell, 1993, vol. 72, pp. 835-846.

```
GCGGACACTCCTCTCGGCTCCTCCCCGGCAGCGGCGGCGGCTCGGAGCGGGCTCCGGGG
CTCGGGTGCAGCGGCCAGCGGGCCTGGCGGCGAGGATTACCCGGGGAAGTGGTTGTCTC
CTGGCTGGAGCCGCGAGACGGGCGCTCAGGGCGCGGGGCCGGCGGCGGCGAACGAGAG
GACGGACTCTGGCGGCCGGGTCGTTGGCCGGGGGAGCGCGGGCACCGGGCGAGCAGGC
CGCGTCGCGCTCACCATGGTCAGCTACTGGGACACCGGGGTCCTGCTGTGCGCGCTGCTC
AGCTGTCTGCTTCTCACAGGATCTAGTTCAGGTTCAAAATTAAAAGATCCTGAACTGAGTTTA
AAAGGCACCCAGCACATCATGCAAGCAGGCCAGACACTGCATCTCCAATGCAGGGGGGAAG
CAGCCCATAAATGGTCTTTGCCTGAAATGGTGAGTAAGGAAAGCGAAAGGCTGAGCATAACT
AAATCTGCCTGTGGAAGAAATGGCAAACAATTCTGCAGTACTTTAACCTTGAACACAGCTCAA
GCAAACCACACTGGCTTCTACAGCTGCAAATATCTAGCTGTACCTACTTCAAAGAAGAAGGA
AACAGAATCTGCAATCTATATATTTATTAGTGATACAGGTAGACCTTTCGTAGAGATGTACAG
TGAAATCCCCGAAATTATACACATGACTGAAGGAAGGGAGCTCGTCATTCCCTGCCGGGTTA
CGTCACCTAACATCACTGTTACTTTAAAAAAGTTTCCACTTGACACTTTGATCCCTGATGGAA
AACGCATAATCTGGGACAGTAGAAAGGGCTTCATCATATCAAATGCAACGTACAAAGAAATA
GGGCTTCTGACCTGTGAAGCAACAGTCAATGGGCATTTGTATAAGACAAACTATCTCACACA
TCGACAAACCAATACAATCATAGATGTCCAAATAAGCACACCACGCCCAGTCAAATTACTTAG
AGGCCATACTCTTGTCCTCAATTGTACTGCTACCACTCCCTTGAACACGAGAGTTCAAATGAC
CTGGAGTTACCCTGATGAAAAAAATAAGAGAGCTTCCGTAAGGCGACGAATTGACCAAAGCA
ATTCCCATGCCAACATATTCTACAGTGTTCTTACTATTGACAAAATGCAGAACAAAGACAAAG
GACTTTATACTTGTCGTGTAAGGAGTGGACCATCATTCAAATCTGTTAACACCTCAGTGCATA
TATATGATAAAGCATTCATCACTGTGAAACATCGAAAACAGCAGGTGCTTGAAACCGTAGCT
GGCAAGCGGTCTTACCGGCTCTCTATGAAAGTGAAGGCATTTCCCTCGCCGGAAGTTGTAT
GGTTAAAAGATGGGTTACCTGCGACTGAGAAATCTGCTCGCTATTTGACTCGTGGCTACTCG
TTAATTATCAAGGACGTAACTGAAGAGGATGCAGGGAATTATACAATCTTGCTGAGCATAAAA
CAGTCAAATGTGTTTAAAAACCTCACTGCCACTCTAATTGTCAATGTGAAACCCCAGATTTAC
GAAAAGGCCGTGTCATCGTTTCCAGACCCGGCTCTCTACCCACTGGGCAGCAGACAAATCC
TGACTTGTACCGCATATGGTATCCCTCAACCTACAATCAAGTGGTTCTGGCACCCCTGTAAC
CATAATCATTCCGAAGCAAGGTGTGACTTTTGTTCCAATAATGAAGAGTCCTTTATCCTGGAT
GCTGACAGCAACATGGGAAACAGAATTGAGAGCATCACTCAGCGCATGGCAATAATAGAAG
GAAAGAATAAGATGGCTAGCACCTTGGTTGTGGCTGACTCTAGAATTTCTGGAATCTACATTT
GCATAGCTTCCAATAAAGTTGGGACTGTGGGAAGAAACATAAGCTTTTATATCACAGATGTG
CCAAATGGGTTTCATGTTAACTTGGAAAAAATGCCGACGGAAGGAGAGGACCTGAAACTGTC
TTGCACAGTTAACAAGTTCTTATACAGAGACGTTACTTGGATTTTTACTGCGGACAGTTAATAA
CAGAACAATGCACTACAGTATTAGCAAGCAAAAATGGCCATCACTAAGGAGCACTCCATCA
CTCTTAATCTTACCATCATGAATGTTTCCCTGCAAGATTCAGGCACCTATGCCTGCAGAGCCA
GGAATGTATACACAGGGGAAGAAATCCTCCAGAAGAAAGAAATTACAATCAGAGGTGAGCAC
TGCAACAAAAAGGCTGTTTTCTCTCGGATCTCCAAATTTAAAAGCACAAGGAATGATTGTACC
ACACAAAGTAATGTAAAACATTAAAGGACTCATTAAAAAGTAACAGTTGTCTCATATCATCTTG
ATTTATTGTCACTGTTGCTAACTTTCAGGCTCGGAGGAGATGCTCCTCCCAAAATGAGTTCG
GAGATGATAGCAGTAATAATGAGACCCCCGGGCTCCAGCTCTGGGCCCCCCATTCAGGCCG
AGGGGGCTGCTCCGGGGGGCCGACTTGGTGCACGTTTGGATTTGGAGGATCCCTGCACTG
CCTTCTCTGTGTTTGTTGCTCTTGCTGTTTTCTCCTGCCTGATAAACAACAACTTGGGATGAT
CCTTTCCATTTTGATGCCAACCTCTTTTTATTTTTAAGCGGCGCCCTATAGT
```
(SEQ. ID. NO.: 5)

FIGURE 2

MVSYWDTGVLLCALLSCLLLTGSSSGSKLKDPELSLKGTQHIMQAGQTLHLQC
RGEAAHKWSLPEMVSKESERLSITKSACGRNGKQFCSTLTLNTAQANHTGFYS
CKYLAVPTSKKKETESAIYIFISDTGRPFVEMYSEIPEIIHMTEGRELVIPCRVTSP
NITVTLKKFPLDTLIPDGKRIIWDSRKGFIISNATYKEIGLLTCEATVNGHLYKTNYL
THRQTNTIIDVQISTPRPVKLLRGHTLVLNCTATTPLNTRVQMTWSYPDEKNKR
ASVRRRIDQSNSHANIFYSVLTIDKMQNKDKGLYTCRVRSGPSFKSVNTSVHIY
DKAFITVKHRKQQVLETVAGKRSYRLSMKVKAFPSPEVVWLKDGLPATEKSAR
YLTRGYSLIIKDVTEEDAGNYTILLSIKQSNVFKNLTATLIVNVKPQIYEKAVSSFP
DPALYPLGSRQILTCTAYGIPQPTIKWFWHPCNHNHSEARCDFCSNNEESFILD
ADSNMGNRIESITQRMAIIEGKNKMASTLVVADSRISGIYICIASNKVGTVGRNISF
YITDVPNGFHVNLEKMPTEGEDLKLSCTVNKFLYRDVTWILLRTVNNRTMHYSIS
KQKMAITKEHSITLNLTIMNVSLQDSGTYACRARNVYTGEEILQKKEITIRGEHCN
KKAVFSRISKFKSTRNDCTTQSNVKH    (SEQ. ID. NO.: 6)

FIGURE 3 kDa

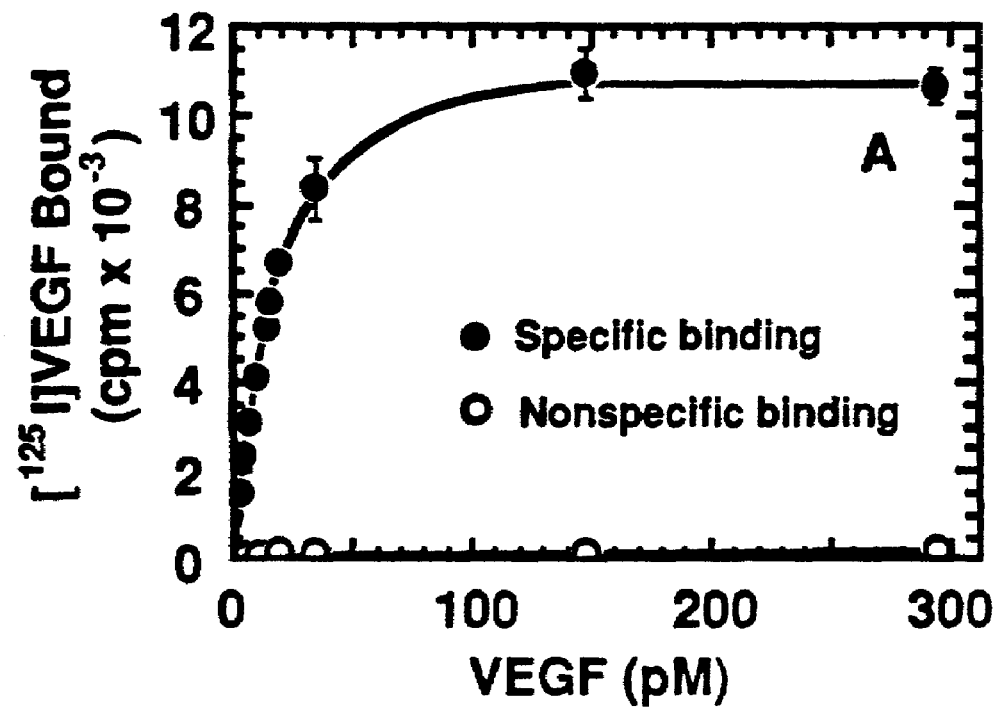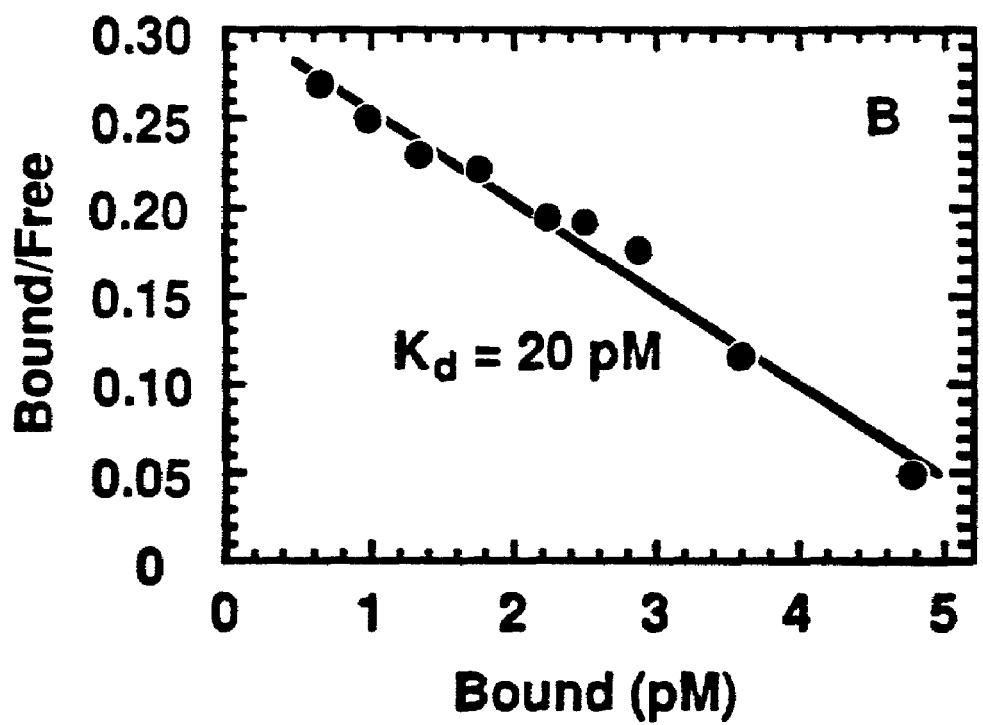
FIGURE 7A & B

```
GGTGTGGTCGCTGCGTTTCCTCTGCCTGCGCCGGGCATCACTTGCGCGCCGCAGAAAGTC
CGTCTGGCAGCCTGGATATCCTCTCCTACCGGCACCCGCAGACGCCCCTGCAGCCGCGGT
CGGCGCCCGGGCTCCCTAGCCCTGTGCGCTCAACTGTCCTGCGCTGCGGGGTGCCGCGAG
TTCCACCTCCGCGCCTCCTTCTCTAGACAGGCGCTGGGAGAAAGAACCGGCTCCCGAGTTC
CGGCATTTCGCCCGGCTCGAGGTGCAGGATGCAGAGCAAGGTGCTGCTGGCCGTCGCCCT
GTGGCTCTGCGTGGAGACCCGGGCCGCCTCTGTGGGTTTGCCTAGTGTTTCTCTTGATCTG
CCCAGGCTCAGCATACAAAAAGACATACTTACAATTAAGGCTAATACAACTCTTCAAATTACT
TGCAGGGGACAGAGGGACTTGGACTGGCTTTGGCCCAATAATCAGAGTGGCAGTGAGCAAA
GGGTGGAGGTGACTGAGTGCAGCGATGGCCTCTTCTGTAAGACACTCACAATTCCAAAAGT
GATCGGAAATGACACTGGAGCCTACAAGTGCTTCTACCGGGAAACTGACTTGGCCTCGGTC
ATTTATGTCTATGTTCAAGATTACAGATCTCCATTTATTGCTTCTGTTAGTGACCAACATGGAG
TCGTGTACATTACTGAGAACAAAAACAAAACTGTGGTGATTCCATGTCTCGGGTCCATTTCAA
ATCTCAACGTGTCACTTTGTGCAAGATACCCAGAAAAGAGATTTGTTCCTGATGGTAACAGAA
TTTCCTGGGACAGCAAGAAGGGCTTTACTATTCCCAGCTACATGATCAGCTATGCTGGCATG
GTCTTCTGTGAAGCAAAAATTAATGATGAAAGTTACCAGTCTATTATGTACATAGTTGTCGTT
GTAGGGTATAGGATTTATGATGTGGTTCTGAGTCCGTCTCATGGAATTGAACTATCTGTTGGA
GAAAAGCTTGTCTTAAATTGTACAGCAAGAACTGAACTAAATGTGGGGATTGACTTCAACTGG
GAATACCCTTCTTCGAAGCATCAGCATAAGAAACTTGTAAACCGAGACCTAAAAACCCAGTCT
GGGAGTGAGATGAAGAAATTTTTGAGCACCTTAACTATAGATGGTGTAACCCGGAGTGACCA
AGGATTGTACACCTGTGCAGCATCCAGTGGGCTGATGACCAAGAAGAACAGCACATTTGTCA
GGGTCCATGAAAAACCTTTTGTTGCTTTTGGAAGTGGCATGGAATCTCTGGTGGAAGCCACG
GTGGGGGAGCGTGTCAGAATCCCTGCGAAGTACCTTGGTTACCCACCCCCAGAAATAAAAT
GGTATAAAAATGGAATACCCCTTGAGTCCAATCACACAATTAAAGCGGGGCATGTACTGACG
ATTATGGAAGTGAGTGAAAGAGACACAGGAAATTACACTGTCATCCTTACCAATCCCATTTCA
AAGGAGAAGCAGAGCCATGTGGTCTCTCTGGTTGTGTATGTCCCACCCCAGATTGGTGAGA
AATCTCTAATCTCTCCTGTGGATTCCTACCAGTACGGCACCACTCAAACGCTGACATGTACG
GTCTATGCCATTCCTCCCCCGCATCACATCCACTGGTATTGGCAGTTGGAGGAAGAGTGCG
CCAACGAGCCCAGCCAAGCTGTCTCAGTGACAAACCCATACCCTTGTGAAGAATGGAGAAG
TGTGGAGGACTTCCAGGGAGGAAATAAAATTGCCGTTAATAAAAATCAATTTGCTCTAATTGA
AGGAAAAAACAAAACTGTAAGTACCCTTGTTATCCAAGCGGCAAATGTGTCAGCTTTGTACAA
ATGTGAAGCGGTCAACAAAGTCGGGAGAGGAGAGAGGGTGATCTCCTTCCACGTGACCAGG
GGTCCTGAAATTACTTTGCAACCTGACATGCAGCCCACTGAGCAGGAGAGCGTGTCTTTGTG
GTGCACTGCAGACAGATCTACGTTTGAGAACCTCACATGGTACAAGCTTGGCCCACAGCCTC
TGCCAATCCATGTGGGAGAGTTGCCCACACCTGTTTGCAAGAACTTGGATACTCTTTGGAAA
TTGAATGCCACCATGTTCTCTAATAGCACAAATGACATTTTGATCATGGAGCTTAAGAATGCA
TCCTTGCAGGACCAAGGAGACTATGTCTGCCTTGCTCAAGACAGGAAGACCAAGAAAAGAC
ATTGCGTGGTCAGGCAGCTCACAGTCCTAGAGCGTTAA       (SEQ. ID. NO.: 16)
```

FIGURE 10

MQSKVLLAVALWLCVETRAASVGLPSVSLDLPRLSIQKDILTIKANTTLQITCRGQ
RDLDWLWPNNQSGSEQRVEVTECSDGLFCKTLTIPKVIGNDTGAYKCFYRETD
LASVIYVYVQDYRSPFIASVSDQHGVVYITENKNKTVVIPCLGSISNLNVSLCARY
PEKRFVPDGNRISWDSKKGFTIPSYMISYAGMVFCEAKINDESYQSIMYIVVVG
YRIYDVVLSPSHGIELSVGEKLVLNCTARTELNVGIDFNWEYPSSKHQHKKLVN
RDLKTQSGSEMKKFLSTLTIDGVTRSDQGLYTCAASSGLMTKKNSTFVRVHEK
PFVAFGSGMESLVEATVGERVRIPAKYLGYPPPEIKWYKNGIPLESNHTIKAGHV
LTIMEVSERDTGNYTVILTNPISKEKQSHVVSLVVYVPPQIGEKSLISPVDSYQYG
TTQTLTCTVYAIPPPHHIHWYWQLEEECANEPSQAVSVTNPYPCEEWRSVEDF
QGGNKIAVNKNQFALIEGKNKTVSTLVIQAANVSALYKCEAVNKVGRGERVISFH
VTRGPEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTKKRH
CVVRQLTVLER... (SEQ. ID. NO.: 13)

FIGURE 11

```
GGTGTGGTCGCTGCGTTTCCTCTGCCTGCGCCGGGCATCACTTGCGCGCCGCAGAAAGTC
CGTCTGGCAGCCTGGATATCCTCTCCTACCGGCACCCGCAGACGCCCCTGCAGCCGCGGT
CGGCGCCCGGGCTCCCTAGCCCTGTGCGCTCAACTGTCCTGCGCTGCGGGGTGCCGCGAG
TTCCACCTCCGCGCCTCCTTCTCTAGACAGGCGCTGGGAGAAAGAACCGGCTCCCGAGTTC
CGGCATTTCGCCCGGCTCGAGGTGCAGGATGCAGAGCAAGGTGCTGCTGGCCGTCGCCCT
GTGGCTCTGCGTGGAGACCCGGGCCGCCTCTGTGGGTTTGCCTAGTGTTTCTCTTGATCTG
CCCAGGCTCAGCATACAAAAAGACATACTTACAATTAAGGCTAATACAACTCTTCAAATTACT
TGCAGGGGACAGAGGGACTTGGACTGGCTTTGGCCCAATAATCAGAGTGGCAGTGAGCAAA
GGGTGGAGGTGACTGAGTGCAGCGATGGCCTCTTCTGTAAGACACTCACAATTCCAAAAGT
GATCGGAAATGACACTGGAGCCTACAAGTGCTTCTACCGGGAAACTGACTTGGCCTCGGTC
ATTTATGTCTATGTTCAAGATTACAGATCTCCATTTATTGCTTCTGTTAGTGACCAACATGGAG
TCGTGTACATTACTGAGAACAAAAACAAAACTGTGGTGATTCCATGTCTCGGGTCCATTTCAA
ATCTCAACGTGTCACTTTGTGCAAGATACCCAGAAAAGAGATTTGTTCCTGATGGTAACAGAA
TTTCCTGGGACAGCAAGAAGGGCTTTACTATTCCCAGCTACATGATCAGCTATGCTGGCATG
GTCTTCTGTGAAGCAAAAATTAATGATGAAAGTTACCAGTCTATTATGTACATAGTTGTCGTT
GTAGGGTATAGGATTTATGATGTGGTTCTGAGTCCGTCTCATGGAATTGAACTATCTGTTGGA
GAAAAGCTTGTCTTAAATTGTACAGCAAGAACTGAACTAAATGTGGGGATTGACTTCAACTGG
GAATACCCTTCTTCGAAGCATCAGCATAAGAAACTTGTAAACCGAGACCTAAAAACCCAGTCT
GGGAGTGAGATGAAGAAATTTTTGAGCACCTTAACTATAGATGGTGTAACCCGGAGTGACCA
AGGATTGTACACCTGTGCAGCATCCAGTGGGCTGATGACCAAGAAGAACAGCACATTTGTCA
GGGTCCATGAAAAACCTTTTGTTGCTTTTGGAAGTGGCATGGAATCTCTGGTGGAAGCCACG
GTGGGGGAGCGTGTCAGAATCCCTGCGAAGTACCTTGGTTACCCACCCCCAGAAATAAAAT
GGTATAAAAATGGAATACCCCTTGAGTCCAATCACACAATTAAAGCGGGGCATGTACTGACG
ATTATGGAAGTGAGTGAAAGAGACACAGGAAATTACACTGTCATCCTTACCAATCCCATTTCA
AAGGAGAAGCAGAGCCATGTGGTCTCTCTGGTTGTGTATGTCCCACCCCAGATTGGTGAGA
AATCTCTAATCTCTCCTGTGGATTCCTACCAGTACGGCACCACTCAAACGCTGACATGTACG
GTCTATGCCATTCCTCCCCCGCATCACATCCACTGGTATTGGCAGTTGGAGGAAGAGTGCG
CCAACGAGCCCAGCCAAGCTGTCTCAGTGACAAACCCATACCCTTGTGAAGAATGGAGAAG
TGTGGAGGACTTCCAGGGAGGAAATAAAATTGCCGTTAATAAAAATCAATTTGCTCTAATTGA
AGGAAAAAACAAAACTGTAAGTACCCTTGTTATCCAAGCGGCAAATGTGTCAGCTTTGTACAA
ATGTGAAGCGGTCAACAAAGTCGGGAGAGGAGAGAGGGTGATCTCCTTCCACGTGACCAGG
GGTCCTGAAATTACTTTGCAACCTGACATGCAGCCCACTGAGCAGGAGAGCGTGTCTTTGTG
GTGCACTGCAGACAGATCTACGTTTGAGAACCTCACATGGTACAAGCTTGGCCCACAGCCTC
TGCCAATCCATGTGGGAGAGTTGCCCACACCTGTTTGCAAGAACTTGGATACTCTTTGGAAA
TTGAATGCCACCATGTTCTCTAATAGCACAAATGACATTTTGATCATGGAGCTTAAGAATGCA
TCCTTGCAGGACCAAGGAGACTATGTCTGCCTTGCTCAAGACAGGAAGACCAAGAAAAGAC
ATTGCGTGGTCAGGCAGCTCACAGTCCTAGAGCGTGTGGCACCCACGATCACAGGAAACCT
GGAGAATCAGACGACAAGTATTGGGGAAAGCATCGAAGTCTCATGCACGGCATCTGGGAAT
CCCCCTCCACAGATCATGTGGTTTAAAGATAATGAGACCCTTGTAGAAGACTCAGGCATTGT
ATTGAAGGATGGGAACCGGAACCTCACTATCCGCAGAGTGAGGAAGGAGGACGAAGGCCT
CTACACCTGCCAGGCATGCAGTGTTCTTGGCTGTGCAAAAGTGGAGGCATTTTTCATAATAG
AAGGTGCCCAGGAAAAGACGAACTTGGAAATCATTATTCTAGTAGGCACGACGGTGATTGCC
ATGTTCTTCTGGCTACTTCTTGTCATCATCCTAGGGACCGTTTAA (SEQ ID.NO.: 18)
```

FIGURE 12

MQSKVLLAVALWLCVETRAASVGLPSVSLDLPRLSIQKDILTIKANTTLQITCRGQ
RDLDWLWPNNQSGSEQRVEVTECSDGLFCKTLTIPKVIGNDTGAYKCFYRETD
LASVIYVYVQDYRSPFIASVSDQHGVVYITENKNKTVVIPCLGSISNLNVSLCARY
PEKRFVPDGNRISWDSKKGFTIPSYMISYAGMVFCEAKINDESYQSIMYIVVVVG
YRIYDVVLSPSHGIELSVGEKLVLNCTARTELNVGIDFNWEYPSSKHQHKKLVN
RDLKTQSGSEMKKFLSTLTIDGVTRSDQGLYTCAASSGLMTKKNSTFVRVHEK
PFVAFGSGMESLVEATVGERVRIPAKYLGYPPPEIKWYKNGIPLESNHTIKAGHV
LTIMEVSERDTGNYTVILTNPISKEKQSHVVSLVVYVPPQIGEKSLISPVDSYQYG
TTQTLTCTVYAIPPPHHIHWYWQLEEECANEPSQAVSVTNPYPCEEWRSVEDF
QGGNKIAVNKNQFALIEGKNKTVSTLVIQAANVSALYKCEAVNKVGRGERVISFH
VTRGPEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTKKRH
CVVRQLTVLERVAPTITGNLENQTTSIGESIEVSCTASGNPPPQIMWFKDNETLV
EDSGIVLKDGNRNLTIRRVRKEDEGLYTCQACSVLGCAKVEAFFIIEGAQEKTNL
EIIILVGTTVIAMFFWLLLVIILGTV... (SEQ. ID. NO.: 15)

FIGURE 13

```
GCGCTCACCATGGTCAGCTACTGGGACACCGGGGTCCTGCTGTGCGCGCTGCTCAGCTGT
CTGCTTCTCACAGGATCTAGTTCAGGTTCAAAATTAAAAGATCCTGAACTGAGTTTAAAAGGC
ACCCAGCACATCATGCAAGCAGGCCAGACACTGCATCTCCAATGCAGGGGGGAAGCAGCC
CATAAATGGTCTTTGCCTGAAATGGTGAGTAAGGAAAGCGAAAGGCTGAGCATAACTAAATC
TGCCTGTGGAAGAAATGGCAAACAATTCTGCAGTACTTTAACCTTGAACACAGCTCAAGCAA
ACCACACTGGCTTCTACAGCTGCAAATATCTAGCTGTACCTACTTCAAAGAAGAAGGAAACA
GAATCTGCAATCTATATATTTATTAGTGATACAGGTAGACCTTTCGTAGAGATGTACAGTGAA
ATCCCCGAAATTATACACATGACTGAAGGAAGGGAGCTCGTCATTCCCTGCCGGGTTACGTC
ACCTAACATCACTGTTACTTTAAAAAAGTTTCCACTTGACACTTTGATCCCTGATGGAAAACG
CATAATCTGGGACAGTAGAAAGGGCTTCATCATATCAAATGCAACGTACAAAGAAATAGGGC
TTCTGACCTGTGAAGCAACAGTCAATGGGCATTTGTATAAGACAAACTATCTCACACATCGAC
AAACCAATACAATCATAGATGTCCAAATAAGCACACCACGCCCAGTCAAATTACTTAGAGGC
CATACTCTTGTCCTCAATTGTACTGCTACCACTCCCTTGAACACGAGAGTTCAAATGACCTGG
AGTTACCCTGATGAAAAAAATAAGAGAGCTTCCGTAAGGCGACGAATTGACCAAAGCAATTC
CCATGCCAACATATTCTACAGTGTTCTTACTATTGACAAAATGCAGAACAAAGACAAAGGACT
TTATACTTGTCGTGTAAGGAGTGGACCATCATTCAAATCTGTTAACACCTCAGTGCATATATA
TGATAAAGCATTCATCACTGTGAAACATCGAAAACAGCAGGTGCTTGAAACCGTAGCTGGCA
AGCGGTCTTACCGGCTCTCTATGAAAGTGAAGGCATTTCCCTCGCCGGAAGTTGTATGGTTA
AAAGATGGGTTACCTGCGACTGAGAAATCTGCTCGCTATTTGACTCGTGGCTACTCGTTAAT
TATCAAGGACGTAACTGAAGAGGATGCAGGGAATTATACAATCTTGCTGAGCATAAAACAGT
CAAATGTGTTTAAAAACCTCACTGCCACTCTAATTGTCAATGTGAAACCCCAGATTTACGAAA
AGGCCGTGTCATCGTTTCCAGACCCGGCTCTCTACCCACTGGGCAGCAGACAAATCCTGAC
TTGTACCGCATATGGTATCCCTCAACCTACAATCAAGTGGTTCTGGCACCCCTGTAACCATAA
TCATTCCGAAGCAAGGTGTGACTTTTGTTCCAATAATGAAGAGTCCTTTATCCTGGATGCTGA
CAGCAACATGGGAAACAGAATTGAGAGCATCACTCAGCGCATGGCAATAATAGAAGGAAAG
AATAAGATGGCTAGCACCTTGGTTGTGGCTGACTCTAGAATTTCTGGAATCTACATTTGCATA
GCTTCCAATAAAGTTGGGACTGTGGGAAGAAACATAAGCTTTTATATCACAGATGTGCCAAAT
GGGTTTCATGTTAACTTGGAAAAAATGCCGACGGAAGGAGAGGACCTGAAACTGTCTTGCAC
AGTTAACAAGTTCTTATACAGAGACGTTACTTGGATTTTACTGCGGACAGTTAATAACAGAAC
AATGCACTACAGTATTAGCAAGCAAAAATGGCCATCACTAAGGAGCACTCCATCACTCTTAA
TCTTACCATCATGAATGTTTCCCTGCAAGATTCAGGCACCTATGCCTGCAGAGCCAGGAATG
TATACACAGGGGAAGAAATCCTCCAGAAGAAAGAAATTACAATCAGAGATCAGGAAGCACCA
TACCTCCTGCGAAACCTCAGTGATCACACAGTGGCCATCAGCAGTTCCACCACTTTAGACTG
TCATGCTAATGGTGTCCCCGAGCCTCAGATCACTTGGTTTAAAAACAACCACAAAATACAACA
AGAGCCTGGAATTATTTTAGGACCAGGAAGCAGCACGCTGTTTATTGAAAGAGTCACAGAAG
AGGATGAAGGTGTCTATCACTGCAAAGCCACCAACCAGAAGGGCTCTGTGGAAAGTTCAGC
ATACCTCACTGTTCAAGGAACCTCGGACAAGTCTAATCTGGAGCTGATCACTCTAACATGCA
CCTGTGTGGCTGCGACTCTCTTCTGGCTCCTATTAACCCTCCTTATCTAA (SEQ.ID.NO.: 17)
```

FIGURE 14

MVSYWDTGVLLCALLSCLLLTGSSSGSKLKDPELSLKGTQHIMQAGQTLHLQC
RGEAAHKWSLPEMVSKESERLSITKSACGRNGKQFCSTLTLNTAQANHTGFYS
CKYLAVPTSKKKETESAIYIFISDTGRPFVEMYSEIPEIIHMTEGRELVIPCRVTSP
NITVTLKKFPLDTLIPDGKRIIWDSRKGFIISNATYKEIGLLTCEATVNGHLYKTNYL
THRQTNTIIDVQISTPRPVKLLRGHTLVLNCTATTPLNTRVQMTWSYPDEKNKR
ASVRRRIDQSNSHANIFYSVLTIDKMQNKDKGLYTCRVRSGPSFKSVNTSVHIY
DKAFITVKHRKQQVLETVAGKRSYRLSMKVKAFPSPEVVWLKDGLPATEKSAR
YLTRGYSLIIKDVTEEDAGNYTILLSIKQSNVFKNLTATLIVNVKPQIYEKAVSSFP
DPALYPLGSRQILTCTAYGIPQPTIKWFWHPCNHNHSEARCDFCSNNEESFILD
ADSNMGNRIESITQRMAIIEGKNKMASTLVVADSRISGIYICIASNKVGTVGRNISF
YITDVPNGFHVNLEKMPTEGEDLKLSCTVNKFLYRDVTWILLRTVNNRTMHYSIS
KQKMAITKEHSITLNLTIMNVSLQDSGTYACRARNVYTGEEILQKKEITIRDQEAP
YLLRNLSDHTVAISSSTTLDCHANGVPEPQITWFKNNHKIQQEPGIILGPGSSTLF
IERVTEEDEGVYHCKATNQKGSVESSAYLTVQGTSDKSNLELITLTCTCVAATLF
WLLLTLLI  (SEQ. ID. NO.:14)

FIGURE 15

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
gcaccttggt tgtggctgac                                              20

<210> SEQ ID NO 2
<211> LENGTH: 25
<212> TYPE: DNA
<213> ORGANISM: Artificial Sequence
<220> FEATURE:
<223> OTHER INFORMATION: oligonucleotide

<400> SEQUENCE: 2
tggaattcgt gctgcttcct ggtcc                                        25

<210> SEQ ID NO 3
<211> LENGTH: 26
<212> TYPE: DNA
<213> ORGANISM: Artificial Sequence
<220> FEATURE:
<223> OTHER INFORMATION: oligonucleotide

<400> SEQUENCE: 3
ggaattccgc gctcaccatg gtcagc                                       26

<210> SEQ ID NO 4
<211> LENGTH: 27
<212> TYPE: DNA
<213> ORGANISM: Artificial Sequence
<220> FEATURE:
<223> OTHER INFORMATION: oligonucleotide

<400> SEQUENCE: 4
tttgaattca cccggcaggg aatgacg                                      27

<210> SEQ ID NO 5
<211> LENGTH: 2651
<212> TYPE: DNA
<213> ORGANISM: Homo sapien
<220> FEATURE:
<221> NAME/KEY: CDS
<222> LOCATION: (250)...(2313)

<400> SEQUENCE: 5
```

-continued

```
gcggacactc ctctcggctc ctccccggca gcggcggcgg ctcggagcgg gctccggggc      60
tcgggtgcag cggccagcgg gcctggcggc gaggattacc cggggaagtg gttgtctcct     120
ggctggagcc gcgagacggg cgctcagggc gcggggccgg cggcggcgaa cgagaggacg     180
gactctggcg gccgggtcgt tggccggggg agcgcgggca ccgggcgagc aggccgcgtc     240 gcgctcacc atg gtc agc tac tgg gac acc ggg gtc ctg ctg tgc gcg ctg    291
          Met Val Ser Tyr Trp Asp Thr Gly Val Leu Leu Cys Ala Leu
            1               5                  10 ctc agc tgt ctg ctt ctc aca gga tct agt tca ggt tca aaa tta aaa      339
Leu Ser Cys Leu Leu Leu Thr Gly Ser Ser Ser Gly Ser Lys Leu Lys
 15              20                  25                  30 gat cct gaa ctg agt tta aaa ggc acc cag cac atc atg caa gca ggc      387
Asp Pro Glu Leu Ser Leu Lys Gly Thr Gln His Ile Met Gln Ala Gly
                 35                  40                  45 cag aca ctg cat ctc caa tgc agg ggg gaa gca gcc cat aaa tgg tct      435
Gln Thr Leu His Leu Gln Cys Arg Gly Glu Ala Ala His Lys Trp Ser
             50                  55                  60 ttg cct gaa atg gtg agt aag gaa agc gaa agg ctg agc ata act aaa      483
Leu Pro Glu Met Val Ser Lys Glu Ser Glu Arg Leu Ser Ile Thr Lys
         65                  70                  75 tct gcc tgt gga aga aat ggc aaa caa ttc tgc agt act tta acc ttg      531
Ser Ala Cys Gly Arg Asn Gly Lys Gln Phe Cys Ser Thr Leu Thr Leu
     80                  85                  90 aac aca gct caa gca aac cac act ggc ttc tac agc tgc aaa tat cta      579
Asn Thr Ala Gln Ala Asn His Thr Gly Phe Tyr Ser Cys Lys Tyr Leu
 95                 100                 105                 110 gct gta cct act tca aag aag aag gaa aca gaa tct gca atc tat ata      627
Ala Val Pro Thr Ser Lys Lys Lys Glu Thr Glu Ser Ala Ile Tyr Ile
                115                 120                 125 ttt att agt gat aca ggt aga cct ttc gta gag atg tac agt gaa atc      675
Phe Ile Ser Asp Thr Gly Arg Pro Phe Val Glu Met Tyr Ser Glu Ile
             130                 135                 140 ccc gaa att ata cac atg act gaa gga agg gag ctc gtc att ccc tgc      723
Pro Glu Ile Ile His Met Thr Glu Gly Arg Glu Leu Val Ile Pro Cys
         145                 150                 155 cgg gtt acg tca cct aac atc act gtt act tta aaa aag ttt cca ctt      771
Arg Val Thr Ser Pro Asn Ile Thr Val Thr Leu Lys Lys Phe Pro Leu
 160                 165                 170 gac act ttg atc cct gat gga aaa cgc ata atc tgg gac agt aga aag      819
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc      867
Gly Phe Ile Ile Ser Asn Ala Thr Tyr Lys Glu Ile Gly Leu Leu Thr
                195                 200                 205 tgt gaa gca aca gtc aat ggg cat ttg tat aag aca aac tat ctc aca      915
Cys Glu Ala Thr Val Asn Gly His Leu Tyr Lys Thr Asn Tyr Leu Thr
             210                 215                 220 cat cga caa acc aat aca atc ata gat gtc caa ata agc aca cca cgc      963
His Arg Gln Thr Asn Thr Ile Ile Asp Val Gln Ile Ser Thr Pro Arg
         225                 230                 235 cca gtc aaa tta ctt aga ggc cat act ctt gtc ctc aat tgt act gct     1011
Pro Val Lys Leu Leu Arg Gly His Thr Leu Val Leu Asn Cys Thr Ala
 240                 245                 250 acc act ccc ttg aac acg aga gtt caa atg acc tgg agt tac cct gat     1059
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat     1107
Glu Lys Asn Lys Arg Ala Ser Val Arg Arg Arg Ile Asp Gln Ser Asn
```

```
                         275                 280                 285
tcc cat gcc aac ata ttc tac agt gtt ctt act att gac aaa atg cag        1155
Ser His Ala Asn Ile Phe Tyr Ser Val Leu Thr Ile Asp Lys Met Gln
            290                 295                 300 aac aaa gac aaa gga ctt tat act tgt cgt gta agg agt gga cca tca        1203
Asn Lys Asp Lys Gly Leu Tyr Thr Cys Arg Val Arg Ser Gly Pro Ser
        305                 310                 315 ttc aaa tct gtt aac acc tca gtg cat ata tat gat aaa gca ttc atc        1251
Phe Lys Ser Val Asn Thr Ser Val His Ile Tyr Asp Lys Ala Phe Ile
    320                 325                 330 act gtg aaa cat cga aaa cag cag gtg ctt gaa acc gta gct ggc aag        1299
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa        1347
Arg Ser Tyr Arg Leu Ser Met Lys Val Lys Ala Phe Pro Ser Pro Glu
                355                 360                 365 gtt gta tgg tta aaa gat ggg tta cct gcg act gag aaa tct gct cgc        1395
Val Val Trp Leu Lys Asp Gly Leu Pro Ala Thr Glu Lys Ser Ala Arg
            370                 375                 380 tat ttg act cgt ggc tac tcg tta att atc aag gac gta act gaa gag        1443
Tyr Leu Thr Arg Gly Tyr Ser Leu Ile Ile Lys Asp Val Thr Glu Glu
        385                 390                 395 gat gca ggg aat tat aca atc ttg ctg agc ata aaa cag tca aat gtg        1491
Asp Ala Gly Asn Tyr Thr Ile Leu Leu Ser Ile Lys Gln Ser Asn Val
    400                 405                 410 ttt aaa aac ctc act gcc act cta att gtc aat gtg aaa ccc cag att        1539
Phe Lys Asn Leu Thr Ala Thr Leu Ile Val Asn Val Lys Pro Gln Ile
415                 420                 425                 430 tac gaa aag gcc gtg tca tcg ttt cca gac ccg gct ctc tac cca ctg        1587
Tyr Glu Lys Ala Val Ser Ser Phe Pro Asp Pro Ala Leu Tyr Pro Leu
                435                 440                 445 ggc agc aga caa atc ctg act tgt acc gca tat ggt atc cct caa cct        1635
Gly Ser Arg Gln Ile Leu Thr Cys Thr Ala Tyr Gly Ile Pro Gln Pro
            450                 455                 460 aca atc aag tgg ttc tgg cac ccc tgt aac cat aat cat tcc gaa gca        1683
Thr Ile Lys Trp Phe Trp His Pro Cys Asn His Asn His Ser Glu Ala
        465                 470                 475 agg tgt gac ttt tgt tcc aat aat gaa gag tcc ttt atc ctg gat gct        1731
Arg Cys Asp Phe Cys Ser Asn Asn Glu Glu Ser Phe Ile Leu Asp Ala
    480                 485                 490 gac agc aac atg gga aac aga att gag agc atc act cag cgc atg gca        1779
Asp Ser Asn Met Gly Asn Arg Ile Glu Ser Ile Thr Gln Arg Met Ala
495                 500                 505                 510 ata ata gaa gga aag aat aag atg gct agc acc ttg gtt gtg gct gac        1827
Ile Ile Glu Gly Lys Asn Lys Met Ala Ser Thr Leu Val Val Ala Asp
                515                 520                 525 tct aga att tct gga atc tac att tgc ata gct tcc aat aaa gtt ggg        1875
Ser Arg Ile Ser Gly Ile Tyr Ile Cys Ile Ala Ser Asn Lys Val Gly
            530                 535                 540 act gtg gga aga aac ata agc ttt tat atc aca gat gtg cca aat ggg        1923
Thr Val Gly Arg Asn Ile Ser Phe Tyr Ile Thr Asp Val Pro Asn Gly
        545                 550                 555 ttt cat gtt aac ttg gaa aaa atg ccg acg gaa gga gag gac ctg aaa        1971
Phe His Val Asn Leu Glu Lys Met Pro Thr Glu Gly Glu Asp Leu Lys
    560                 565                 570 ctg tct tgc aca gtt aac aag ttc tta tac aga gac gtt act tgg att        2019
Leu Ser Cys Thr Val Asn Lys Phe Leu Tyr Arg Asp Val Thr Trp Ile
575                 580                 585                 590 tta ctg cgg aca gtt aat aac aga aca atg cac tac agt att agc aag        2067
```

-continued

| | | | | | | | | | | | | |
|---|---|---|---|---|---|---|---|---|---|---|---|---|
|Leu|Leu|Arg|Thr|Val|Asn|Asn|Arg|Thr|Met|His|Tyr|Ser Ile Ser Lys|
| | | |595| | | |600| | | |605| |

```
caa aaa atg gcc atc act aag gag cac tcc atc act ctt aat ctt acc    2115
Gln Lys Met Ala Ile Thr Lys Glu His Ser Ile Thr Leu Asn Leu Thr
            610                 615                 620 atc atg aat gtt tcc ctg caa gat tca ggc acc tat gcc tgc aga gcc    2163
Ile Met Asn Val Ser Leu Gln Asp Ser Gly Thr Tyr Ala Cys Arg Ala
            625                 630                 635 agg aat gta tac aca ggg gaa gaa atc ctc cag aag aaa gaa att aca    2211
Arg Asn Val Tyr Thr Gly Glu Glu Ile Leu Gln Lys Lys Glu Ile Thr
            640                 645                 650 atc aga ggt gag cac tgc aac aaa aag gct gtt ttc tct cgg atc tcc    2259
Ile Arg Gly Glu His Cys Asn Lys Lys Ala Val Phe Ser Arg Ile Ser
655                 660                 665                 670 aaa ttt aaa agc aca agg aat gat tgt acc aca caa agt aat gta aaa    2307
Lys Phe Lys Ser Thr Arg Asn Asp Cys Thr Thr Gln Ser Asn Val Lys
                675                 680                 685 cat taa aggactcatt aaaaagtaac agttgtctca tatcatcttg atttattgtc    2363
His * actgttgcta actttcaggc tcggaggaga tgctcctccc aaaatgagtt cggagatgat    2423
agcagtaata atgagacccc cgggctccag ctctgggccc ccattcagg ccgaggggc     2483 tgctccgggg ggccgacttg gtgcacgttt ggatttggag gatccctgca ctgccttctc    2543
tgtgtttgtt gctcttgctg ttttctcctg cctgataaac aacaacttgg gatgatcctt    2603
tccattttga tgccaacctc ttttttatttt taagcggcgc cctatagt                2651

<210> SEQ ID NO 6
<211> LENGTH: 687
<212> TYPE: PRT
<213> ORGANISM: Homo sapien

<400> SEQUENCE: 6
```

| | | | | | | | | | | | | | | | |
|---|---|---|---|---|---|---|---|---|---|---|---|---|---|---|---|
|Met|Val|Ser|Tyr|Trp|Asp|Thr|Gly|Val|Leu|Leu|Cys|Ala|Leu|Leu|Ser|
|1| | | |5| | | | |10| | | | |15| |

| | | | | | | | | | | | | | | | |
|---|---|---|---|---|---|---|---|---|---|---|---|---|---|---|---|
|Cys|Leu|Leu|Leu|Thr|Gly|Ser|Ser|Ser|Gly|Ser|Lys|Leu|Lys|Asp|Pro|
| | | |20| | | | |25| | | | |30| | |

| | | | | | | | | | | | | | | | |
|---|---|---|---|---|---|---|---|---|---|---|---|---|---|---|---|
|Glu|Leu|Ser|Leu|Lys|Gly|Thr|Gln|His|Ile|Met|Gln|Ala|Gly|Gln|Thr|
| | | | |35| | | | |40| | | | |45| | |

| | | | | | | | | | | | | | | | |
|---|---|---|---|---|---|---|---|---|---|---|---|---|---|---|---|
|Leu|His|Leu|Gln|Cys|Arg|Gly|Glu|Ala|Ala|His|Lys|Trp|Ser|Leu|Pro|
| | |50| | | | |55| | | | |60| | | |

| | | | | | | | | | | | | | | | |
|---|---|---|---|---|---|---|---|---|---|---|---|---|---|---|---|
|Glu|Met|Val|Ser|Lys|Glu|Ser|Glu|Arg|Leu|Ser|Ile|Thr|Lys|Ser|Ala|
|65| | | | |70| | | | |75| | | | |80|

| | | | | | | | | | | | | | | | |
|---|---|---|---|---|---|---|---|---|---|---|---|---|---|---|---|
|Cys|Gly|Arg|Asn|Gly|Lys|Gln|Phe|Cys|Ser|Thr|Leu|Thr|Leu|Asn|Thr|
| | | | |85| | | | |90| | | | |95| |

| | | | | | | | | | | | | | | | |
|---|---|---|---|---|---|---|---|---|---|---|---|---|---|---|---|
|Ala|Gln|Ala|Asn|His|Thr|Gly|Phe|Tyr|Ser|Cys|Lys|Tyr|Leu|Ala|Val|
| | | |100| | | | |105| | | | |110| | |

| | | | | | | | | | | | | | | | |
|---|---|---|---|---|---|---|---|---|---|---|---|---|---|---|---|
|Pro|Thr|Ser|Lys|Lys|Lys|Glu|Thr|Glu|Ser|Ala|Ile|Tyr|Ile|Phe|Ile|
| | |115| | | | |120| | | | |125| | | |

| | | | | | | | | | | | | | | | |
|---|---|---|---|---|---|---|---|---|---|---|---|---|---|---|---|
|Ser|Asp|Thr|Gly|Arg|Pro|Phe|Val|Glu|Met|Tyr|Ser|Glu|Ile|Pro|Glu|
| | |130| | | | |135| | | | |140| | | |

| | | | | | | | | | | | | | | | |
|---|---|---|---|---|---|---|---|---|---|---|---|---|---|---|---|
|Ile|Ile|His|Met|Thr|Glu|Gly|Arg|Glu|Leu|Val|Ile|Pro|Cys|Arg|Val|
|145| | | | |150| | | | |155| | | | |160|

| | | | | | | | | | | | | | | | |
|---|---|---|---|---|---|---|---|---|---|---|---|---|---|---|---|
|Thr|Ser|Pro|Asn|Ile|Thr|Val|Thr|Leu|Lys|Lys|Phe|Pro|Leu|Asp|Thr|
| | | | |165| | | | |170| | | | |175| |

| | | | | | | | | | | | | | | | |
|---|---|---|---|---|---|---|---|---|---|---|---|---|---|---|---|
|Leu|Ile|Pro|Asp|Gly|Lys|Arg|Ile|Ile|Trp|Asp|Ser|Arg|Lys|Gly|Phe|
| | | |180| | | | |185| | | | |190| | |

-continued

```
Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
    275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
    435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
    515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
    595                 600                 605
```

```
Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
                660                 665                 670

Lys Ser Thr Arg Asn Asp Cys Thr Thr Gln Ser Asn Val Lys His
        675                 680                 685

<210> SEQ ID NO 7
<211> LENGTH: 37
<212> TYPE: DNA
<213> ORGANISM: Artificial Sequence
<220> FEATURE:
<223> OTHER INFORMATION: oligonucleotide

<400> SEQUENCE: 7
ttttggatcc ctgcagacag atctacgttt gagaacc                              37

<210> SEQ ID NO 8
<211> LENGTH: 32
<212> TYPE: DNA
<213> ORGANISM: Artificial Sequence
<220> FEATURE:
<223> OTHER INFORMATION: oligonucleotide

<400> SEQUENCE: 8
ttttggatcc ttaacgctct aggactgtga gc                                   32

<210> SEQ ID NO 9
<211> LENGTH: 31
<212> TYPE: DNA
<213> ORGANISM: Artificial Sequence
<220> FEATURE:
<223> OTHER INFORMATION: oligonucleotide

<400> SEQUENCE: 9
ttttggatcc aacggtccct aggatgatga c                                    31

<210> SEQ ID NO 10
<211> LENGTH: 23
<212> TYPE: DNA
<213> ORGANISM: Artificial Sequence
<220> FEATURE:
<223> OTHER INFORMATION: oligonucleotide

<400> SEQUENCE: 10
agcaccttgg ttgtggctga ctc                                             23

<210> SEQ ID NO 11
<211> LENGTH: 32
<212> TYPE: DNA
<213> ORGANISM: Artificial Sequence
<220> FEATURE:
<223> OTHER INFORMATION: oligonucleotide

<400> SEQUENCE: 11
ttttggatcc ttagataagg agggttaata gg                                   32

<210> SEQ ID NO 12
<211> LENGTH: 661
<212> TYPE: PRT
```

-continued

<213> ORGANISM: Homo sapien

<400> SEQUENCE: 12

```
Ser Lys Leu Lys Asp Pro Glu Leu Ser Leu Lys Gly Thr Gln His Ile
 1               5                  10                  15
Met Gln Ala Gly Gln Thr Leu His Leu Gln Cys Arg Gly Glu Ala Ala
             20                  25                  30
His Lys Trp Ser Leu Pro Glu Met Val Ser Lys Glu Ser Glu Arg Leu
         35                  40                  45
Ser Ile Thr Lys Ser Ala Cys Gly Arg Asn Gly Lys Gln Phe Cys Ser
 50                  55                  60
Thr Leu Thr Leu Asn Thr Ala Gln Ala Asn His Thr Gly Phe Tyr Ser
 65                  70                  75                  80
Cys Lys Tyr Leu Ala Val Pro Thr Ser Lys Lys Lys Glu Thr Glu Ser
                 85                  90                  95
Ala Ile Tyr Ile Phe Ile Ser Asp Thr Gly Arg Pro Phe Val Glu Met
            100                 105                 110
Tyr Ser Glu Ile Pro Glu Ile Ile His Met Thr Glu Gly Arg Glu Leu
        115                 120                 125
Val Ile Pro Cys Arg Val Thr Ser Pro Asn Ile Thr Val Thr Leu Lys
130                 135                 140
Lys Phe Pro Leu Asp Thr Leu Ile Pro Asp Gly Lys Arg Ile Ile Trp
145                 150                 155                 160
Asp Ser Arg Lys Gly Phe Ile Ile Ser Asn Ala Thr Tyr Lys Glu Ile
                165                 170                 175
Gly Leu Leu Thr Cys Glu Ala Thr Val Asn Gly His Leu Tyr Lys Thr
            180                 185                 190
Asn Tyr Leu Thr His Arg Gln Thr Asn Thr Ile Ile Asp Val Gln Ile
        195                 200                 205
Ser Thr Pro Arg Pro Val Lys Leu Leu Arg Gly His Thr Leu Val Leu
210                 215                 220
Asn Cys Thr Ala Thr Thr Pro Leu Asn Thr Arg Val Gln Met Thr Trp
225                 230                 235                 240
Ser Tyr Pro Asp Glu Lys Asn Lys Arg Ala Ser Val Arg Arg Arg Ile
                245                 250                 255
Asp Gln Ser Asn Ser His Ala Asn Ile Phe Tyr Ser Val Leu Thr Ile
            260                 265                 270
Asp Lys Met Gln Asn Lys Asp Lys Gly Leu Tyr Thr Cys Arg Val Arg
        275                 280                 285
Ser Gly Pro Ser Phe Lys Ser Val Asn Thr Ser Val His Ile Tyr Asp
290                 295                 300
Lys Ala Phe Ile Thr Val Lys His Arg Lys Gln Gln Val Leu Glu Thr
305                 310                 315                 320
Val Ala Gly Lys Arg Ser Tyr Arg Leu Ser Met Lys Val Lys Ala Phe
                325                 330                 335
Pro Ser Pro Glu Val Val Trp Leu Lys Asp Gly Leu Pro Ala Thr Glu
            340                 345                 350
Lys Ser Ala Arg Tyr Leu Thr Arg Gly Tyr Ser Leu Ile Ile Lys Asp
        355                 360                 365
Val Thr Glu Glu Asp Ala Gly Asn Tyr Thr Ile Leu Leu Ser Ile Lys
370                 375                 380
Gln Ser Asn Val Phe Lys Asn Leu Thr Ala Thr Leu Ile Val Asn Val
385                 390                 395                 400
```

```
Lys Pro Gln Ile Tyr Glu Lys Ala Val Ser Ser Phe Pro Asp Pro Ala
                405                 410                 415

Leu Tyr Pro Leu Gly Ser Arg Gln Ile Leu Thr Cys Thr Ala Tyr Gly
            420                 425                 430

Ile Pro Gln Pro Thr Ile Lys Trp Phe Trp His Pro Cys Asn His Asn
            435                 440                 445

His Ser Glu Ala Arg Cys Asp Phe Cys Ser Asn Asn Glu Glu Ser Phe
450                 455                 460

Ile Leu Asp Ala Asp Ser Asn Met Gly Asn Arg Ile Glu Ser Ile Thr
465                 470                 475                 480

Gln Arg Met Ala Ile Glu Gly Lys Asn Lys Met Ala Ser Thr Leu
                485                 490                 495

Val Val Ala Asp Ser Arg Ile Ser Gly Ile Tyr Ile Cys Ile Ala Ser
            500                 505                 510

Asn Lys Val Gly Thr Val Gly Arg Asn Ile Ser Phe Tyr Ile Thr Asp
            515                 520                 525

Val Pro Asn Gly Phe His Val Asn Leu Glu Lys Met Pro Thr Glu Gly
            530                 535                 540

Glu Asp Leu Lys Leu Ser Cys Thr Val Asn Lys Phe Leu Tyr Arg Asp
545                 550                 555                 560

Val Thr Trp Ile Leu Leu Arg Thr Val Asn Asn Arg Thr Met His Tyr
                565                 570                 575

Ser Ile Ser Lys Gln Lys Met Ala Ile Thr Lys Glu His Ser Ile Thr
            580                 585                 590

Leu Asn Leu Thr Ile Met Asn Val Ser Leu Gln Asp Ser Gly Thr Tyr
            595                 600                 605

Ala Cys Arg Ala Arg Asn Val Tyr Thr Gly Glu Glu Ile Leu Gln Lys
            610                 615                 620

Lys Glu Ile Thr Ile Arg Gly Glu His Cys Asn Lys Lys Ala Val Phe
625                 630                 635                 640

Ser Arg Ile Ser Lys Phe Lys Ser Thr Arg Asn Asp Cys Thr Thr Gln
                645                 650                 655

Ser Asn Val Lys His
            660

<210> SEQ ID NO 13
<211> LENGTH: 664
<212> TYPE: PRT
<213> ORGANISM: Homo sapien

<400> SEQUENCE: 13

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110
```

-continued

```
Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
        130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
        210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Ala Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525
```

```
Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg
            660
```

<210> SEQ ID NO 14
<211> LENGTH: 780
<212> TYPE: PRT
<213> ORGANISM: Homo sapien

<400> SEQUENCE: 14

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

-continued

```
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
        370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
    450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
    530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
```

-continued

Asp Gln Glu Ala Pro Tyr Leu Leu Arg Asn Leu Ser Asp His Thr Val
        660                 665                 670

Ala Ile Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
        690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                425                 730                 735

Lys Gly Ser Val Glu Ser Ser Ala Tyr Leu Thr Val Gln Gly Thr Ser
        740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Leu Ile
        770                 775                 780

<210> SEQ ID NO 15
<211> LENGTH: 789
<212> TYPE: PRT
<213> ORGANISM: Homo sapien

<400> SEQUENCE: 15

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

-continued

```
Asp Phe Asn Trp Glu Tyr Pro Ser Ser Lys His Gln His Lys Lys Leu
            260                 265                 270
Val Asn Arg Asp Leu Lys Thr Gln Ser Gly Ser Glu Met Lys Lys Phe
            275                 280                 285
Leu Ser Thr Leu Thr Ile Asp Gly Val Thr Arg Ser Asp Gln Gly Leu
            290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
            340                 345                 350
Lys Tyr Leu Gly Tyr Pro Pro Pro Glu Ile Lys Trp Tyr Lys Asn Gly
            355                 360                 365
Ile Pro Leu Glu Ser Asn His Thr Ile Lys Ala Gly His Val Leu Thr
            370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
            435                 440                 445
Ala Ile Pro Pro Pro His His Ile His Trp Tyr Trp Gln Leu Glu Glu
450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Ala Val Asn Lys Asn Gln Phe Ala Leu Ile Glu Gly Lys Asn Lys
            500                 505                 510
Thr Val Ser Thr Leu Val Ile Gln Ala Ala Asn Val Ser Ala Leu Tyr
            515                 520                 525
Lys Cys Glu Ala Val Asn Lys Val Gly Arg Gly Glu Arg Val Ile Ser
            530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
            595                 600                 605
Leu Trp Lys Leu Asn Ala Thr Met Phe Ser Asn Ser Thr Asn Asp Ile
            610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
            660                 665                 670
```

-continued

```
Leu Glu Asn Gln Thr Thr Ser Ile Gly Glu Ser Ile Glu Val Ser Cys
            675                 680                 685

Thr Ala Ser Gly Asn Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
        755                 760                 765

Val Gly Thr Thr Val Ile Ala Met Phe Phe Trp Leu Leu Leu Val Ile
    770                 775                 780

Ile Leu Gly Thr Val
785
```

<210> SEQ ID NO 16
<211> LENGTH: 2264
<212> TYPE: DNA
<213> ORGANISM: Homo sapien
<220> FEATURE:
<221> NAME/KEY: CDS
<222> LOCATION: (270)...(2264)

<400> SEQUENCE: 16

```
ggtgtggtcg ctgcgtttcc tctgcctgcg ccgggcatca cttgcgcgcc gcagaaagtc     60
cgtctggcag cctggatatc ctctcctacc ggcacccgca gacgcccctg cagccgcggt    120
cggcgcccgg gctccctagc cctgtgcgct caactgtcct gcgctgcggg gtgccgcgag    180
ttccacctcc gcgcctcctt ctctagacag gcgctgggag aaagaaccgg ctcccgagtt    240
ccggcatttc gcccggctcg aggtgcagg atg cag agc aag gtg ctg ctg gcc    293
                                  Met Gln Ser Lys Val Leu Leu Ala
                                   1               5 gtc gcc ctg tgg ctc tgc gtg gag acc cgg gcc gcc tct gtg ggt ttg    341
Val Ala Leu Trp Leu Cys Val Glu Thr Arg Ala Ala Ser Val Gly Leu
 10                  15                  20 cct agt gtt tct ctt gat ctg ccc agg ctc agc ata caa aaa gac ata    389
Pro Ser Val Ser Leu Asp Leu Pro Arg Leu Ser Ile Gln Lys Asp Ile
 25                  30                  35                  40 ctt aca att aag gct aat aca act ctt caa att act tgc agg gga cag    437
Leu Thr Ile Lys Ala Asn Thr Thr Leu Gln Ile Thr Cys Arg Gly Gln
                45                  50                  55 agg gac ttg gac tgg ctt tgg ccc aat aat cag agt ggc agt gag caa    485
Arg Asp Leu Asp Trp Leu Trp Pro Asn Asn Gln Ser Gly Ser Glu Gln
            60                  65                  70 agg gtg gag gtg act gag tgc agc gat ggc ctc ttc tgt aag aca ctc    533
Arg Val Glu Val Thr Glu Cys Ser Asp Gly Leu Phe Cys Lys Thr Leu
        75                  80                  85 aca att cca aaa gtg atc gga aat gac act gga gcc tac aag tgc ttc    581
Thr Ile Pro Lys Val Ile Gly Asn Asp Thr Gly Ala Tyr Lys Cys Phe
    90                  95                 100 tac cgg gaa act gac ttg gcc tcg gtc att tat gtc tat gtt caa gat    629
Tyr Arg Glu Thr Asp Leu Ala Ser Val Ile Tyr Val Tyr Val Gln Asp
105                 110                 115                 120 tac aga tct cca ttt att gct tct gtt agt gac caa cat gga gtc gtg    677
Tyr Arg Ser Pro Phe Ile Ala Ser Val Ser Asp Gln His Gly Val Val
                125                 130                 135
```

```
tac att act gag aac aaa aac aaa act gtg gtg att cca tgt ctc ggg      725
Tyr Ile Thr Glu Asn Lys Asn Lys Thr Val Val Ile Pro Cys Leu Gly
            140                 145                 150 tcc att tca aat ctc aac gtg tca ctt tgt gca aga tac cca gaa aag      773
Ser Ile Ser Asn Leu Asn Val Ser Leu Cys Ala Arg Tyr Pro Glu Lys
        155                 160                 165 aga ttt gtt cct gat ggt aac aga att tcc tgg gac agc aag aag ggc      821
Arg Phe Val Pro Asp Gly Asn Arg Ile Ser Trp Asp Ser Lys Lys Gly
    170                 175                 180 ttt act att ccc agc tac atg atc agc tat gct ggc atg gtc ttc tgt      869
Phe Thr Ile Pro Ser Tyr Met Ile Ser Tyr Ala Gly Met Val Phe Cys
185                 190                 195                 200 gaa gca aaa att aat gat gaa agt tac cag tct att atg tac ata gtt      917
Glu Ala Lys Ile Asn Asp Glu Ser Tyr Gln Ser Ile Met Tyr Ile Val
                205                 210                 215 gtc gtt gta ggg tat agg att tat gat gtg gtt ctg agt ccg tct cat      965
Val Val Val Gly Tyr Arg Ile Tyr Asp Val Val Leu Ser Pro Ser His
            220                 225                 230 gga att gaa cta tct gtt gga gaa aag ctt gtc tta aat tgt aca gca     1013
Gly Ile Glu Leu Ser Val Gly Glu Lys Leu Val Leu Asn Cys Thr Ala
        235                 240                 245 aga act gaa cta aat gtg ggg att gac ttc aac tgg gaa tac cct tct     1061
Arg Thr Glu Leu Asn Val Gly Ile Asp Phe Asn Trp Glu Tyr Pro Ser
    250                 255                 260 tcg aag cat cag cat aag aaa ctt gta aac cga gac cta aaa acc cag     1109
Ser Lys His Gln His Lys Lys Leu Val Asn Arg Asp Leu Lys Thr Gln
265                 270                 275                 280 tct ggg agt gag atg aag aaa ttt ttg agc acc tta act ata gat ggt     1157
Ser Gly Ser Glu Met Lys Lys Phe Leu Ser Thr Leu Thr Ile Asp Gly
                285                 290                 295 gta acc cgg agt gac caa gga ttg tac acc tgt gca gca tcc agt ggg     1205
Val Thr Arg Ser Asp Gln Gly Leu Tyr Thr Cys Ala Ala Ser Ser Gly
            300                 305                 310 ctg atg acc aag aag aac agc aca ttt gtc agg gtc cat gaa aaa cct     1253
Leu Met Thr Lys Lys Asn Ser Thr Phe Val Arg Val His Glu Lys Pro
        315                 320                 325 ttt gtt gct ttt gga agt ggc atg gaa tct ctg gtg gaa gcc acg gtg     1301
Phe Val Ala Phe Gly Ser Gly Met Glu Ser Leu Val Glu Ala Thr Val
    330                 335                 340 ggg gag cgt gtc aga atc cct gcg aag tac ctt ggt tac cca ccc cca     1349
Gly Glu Arg Val Arg Ile Pro Ala Lys Tyr Leu Gly Tyr Pro Pro Pro
345                 350                 355                 360 gaa ata aaa tgg tat aaa aat gga ata ccc ctt gag tcc aat cac aca     1397
Glu Ile Lys Trp Tyr Lys Asn Gly Ile Pro Leu Glu Ser Asn His Thr
                365                 370                 375 att aaa gcg ggg cat gta ctg acg att atg gaa gtg agt gaa aga gac     1445
Ile Lys Ala Gly His Val Leu Thr Ile Met Glu Val Ser Glu Arg Asp
            380                 385                 390 aca gga aat tac act gtc atc ctt acc aat ccc att tca aag gag aag     1493
Thr Gly Asn Tyr Thr Val Ile Leu Thr Asn Pro Ile Ser Lys Glu Lys
        395                 400                 405 cag agc cat gtg gtc tct ctg gtt gtg tat gtc cca ccc cag att ggt     1541
Gln Ser His Val Val Ser Leu Val Val Tyr Val Pro Pro Gln Ile Gly
    410                 415                 420 gag aaa tct cta atc tct cct gtg gat tcc tac cag tac ggc acc act     1589
Glu Lys Ser Leu Ile Ser Pro Val Asp Ser Tyr Gln Tyr Gly Thr Thr
425                 430                 435                 440 caa acg ctg aca tgt acg gtc tat gcc att cct ccc ccg cat cac atc     1637
Gln Thr Leu Thr Cys Thr Val Tyr Ala Ile Pro Pro Pro His His Ile
                445                 450                 455
```

```
cac tgg tat tgg cag ttg gag gaa gag tgc gcc aac gag ccc agc caa    1685
His Trp Tyr Trp Gln Leu Glu Glu Glu Cys Ala Asn Glu Pro Ser Gln
            460                 465                 470 gct gtc tca gtg aca aac cca tac cct tgt gaa gaa tgg aga agt gtg    1733
Ala Val Ser Val Thr Asn Pro Tyr Pro Cys Glu Glu Trp Arg Ser Val
        475                 480                 485 gag gac ttc cag gga gga aat aaa att gcc gtt aat aaa aat caa ttt    1781
Glu Asp Phe Gln Gly Gly Asn Lys Ile Ala Val Asn Lys Asn Gln Phe
    490                 495                 500 gct cta att gaa gga aaa aac aaa act gta agt acc ctt gtt atc caa    1829
Ala Leu Ile Glu Gly Lys Asn Lys Thr Val Ser Thr Leu Val Ile Gln
505                 510                 515                 520 gcg gca aat gtg tca gct ttg tac aaa tgt gaa gcg gtc aac aaa gtc    1877
Ala Ala Asn Val Ser Ala Leu Tyr Lys Cys Glu Ala Val Asn Lys Val
                525                 530                 535 ggg aga gga gag agg gtg atc tcc ttc cac gtg acc agg ggt cct gaa    1925
Gly Arg Gly Glu Arg Val Ile Ser Phe His Val Thr Arg Gly Pro Glu
            540                 545                 550 att act ttg caa cct gac atg cag ccc act gag cag gag agc gtg tct    1973
Ile Thr Leu Gln Pro Asp Met Gln Pro Thr Glu Gln Glu Ser Val Ser
        555                 560                 565 ttg tgg tgc act gca gac aga tct acg ttt gag aac ctc aca tgg tac    2021
Leu Trp Cys Thr Ala Asp Arg Ser Thr Phe Glu Asn Leu Thr Trp Tyr
    570                 575                 580 aag ctt ggc cca cag cct ctg cca atc cat gtg gga gag ttg ccc aca    2069
Lys Leu Gly Pro Gln Pro Leu Pro Ile His Val Gly Glu Leu Pro Thr
585                 590                 595                 600 cct gtt tgc aag aac ttg gat act ctt tgg aaa ttg aat gcc acc atg    2117
Pro Val Cys Lys Asn Leu Asp Thr Leu Trp Lys Leu Asn Ala Thr Met
                605                 610                 615 ttc tct aat agc aca aat gac att ttg atc atg gag ctt aag aat gca    2165
Phe Ser Asn Ser Thr Asn Asp Ile Leu Ile Met Glu Leu Lys Asn Ala
            620                 625                 630 tcc ttg cag gac caa gga gac tat gtc tgc ctt gct caa gac agg aag    2213
Ser Leu Gln Asp Gln Gly Asp Tyr Val Cys Leu Ala Gln Asp Arg Lys
        635                 640                 645 acc aag aaa aga cat tgc gtg gtc agg cag ctc aca gtc cta gag cgt    2261
Thr Lys Lys Arg His Cys Val Val Arg Gln Leu Thr Val Leu Glu Arg
    650                 655                 660 taa                                                                2264
*

<210> SEQ ID NO 17
<211> LENGTH: 2352
<212> TYPE: DNA
<213> ORGANISM: Homo sapien
<220> FEATURE:
<221> NAME/KEY: CDS
<222> LOCATION: (10)...(2352)

<400> SEQUENCE: 17 gcgctcacc atg gtc agc tac tgg gac acc ggg gtc ctg ctg tgc gcg ctg    51
           Met Val Ser Tyr Trp Asp Thr Gly Val Leu Leu Cys Ala Leu
             1               5                  10 ctc agc tgt ctg ctt ctc aca gga tct agt tca ggt tca aaa tta aaa    99
Leu Ser Cys Leu Leu Leu Thr Gly Ser Ser Ser Gly Ser Lys Leu Lys
 15                  20                  25                  30 gat cct gaa ctg agt tta aaa ggc acc cag cac atc atg caa gca ggc    147
Asp Pro Glu Leu Ser Leu Lys Gly Thr Gln His Ile Met Gln Ala Gly
                 35                  40                  45
```

-continued

```
cag aca ctg cat ctc caa tgc agg ggg gaa gca gcc cat aaa tgg tct      195
Gln Thr Leu His Leu Gln Cys Arg Gly Glu Ala Ala His Lys Trp Ser
         50                  55                  60 ttg cct gaa atg gtg agt aag gaa agc gaa agg ctg agc ata act aaa      243
Leu Pro Glu Met Val Ser Lys Glu Ser Glu Arg Leu Ser Ile Thr Lys
 65                  70                  75 tct gcc tgt gga aga aat ggc aaa caa ttc tgc agt act tta acc ttg      291
Ser Ala Cys Gly Arg Asn Gly Lys Gln Phe Cys Ser Thr Leu Thr Leu
         80                  85                  90 aac aca gct caa gca aac cac act ggc ttc tac agc tgc aaa tat cta      339
Asn Thr Ala Gln Ala Asn His Thr Gly Phe Tyr Ser Cys Lys Tyr Leu
 95                 100                 105                 110 gct gta cct act tca aag aag aag gaa aca gaa tct gca atc tat ata      387
Ala Val Pro Thr Ser Lys Lys Lys Glu Thr Glu Ser Ala Ile Tyr Ile
                115                 120                 125 ttt att agt gat aca ggt aga cct ttc gta gag atg tac agt gaa atc      435
Phe Ile Ser Asp Thr Gly Arg Pro Phe Val Glu Met Tyr Ser Glu Ile
        130                 135                 140 ccc gaa att ata cac atg act gaa gga agg gag ctc gtc att ccc tgc      483
Pro Glu Ile Ile His Met Thr Glu Gly Arg Glu Leu Val Ile Pro Cys
                145                 150                 155 cgg gtt acg tca cct aac atc act gtt act tta aaa aag ttt cca ctt      531
Arg Val Thr Ser Pro Asn Ile Thr Val Thr Leu Lys Lys Phe Pro Leu
        160                 165                 170 gac act ttg atc cct gat gga aaa cgc ata atc tgg gac agt aga aag      579
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc      627
Gly Phe Ile Ile Ser Asn Ala Thr Tyr Lys Glu Ile Gly Leu Leu Thr
                195                 200                 205 tgt gaa gca aca gtc aat ggg cat ttg tat aag aca aac tat ctc aca      675
Cys Glu Ala Thr Val Asn Gly His Leu Tyr Lys Thr Asn Tyr Leu Thr
        210                 215                 220 cat cga caa acc aat aca atc ata gat gtc caa ata agc aca cca cgc      723
His Arg Gln Thr Asn Thr Ile Ile Asp Val Gln Ile Ser Thr Pro Arg
                225                 230                 235 cca gtc aaa tta ctt aga ggc cat act ctt gtc ctc aat tgt act gct      771
Pro Val Lys Leu Leu Arg Gly His Thr Leu Val Leu Asn Cys Thr Ala
        240                 245                 250 acc act ccc ttg aac acg aga gtt caa atg acc tgg agt tac cct gat      819
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat      867
Glu Lys Asn Lys Arg Ala Ser Val Arg Arg Arg Ile Asp Gln Ser Asn
                275                 280                 285 tcc cat gcc aac ata ttc tac agt gtt ctt act att gac aaa atg cag      915
Ser His Ala Asn Ile Phe Tyr Ser Val Leu Thr Ile Asp Lys Met Gln
        290                 295                 300 aac aaa gac aaa gga ctt tat act tgt cgt gta agg agt gga cca tca      963
Asn Lys Asp Lys Gly Leu Tyr Thr Cys Arg Val Arg Ser Gly Pro Ser
        305                 310                 315 ttc aaa tct gtt aac acc tca gtg cat ata tat gat aaa gca ttc atc     1011
Phe Lys Ser Val Asn Thr Ser Val His Ile Tyr Asp Lys Ala Phe Ile
        320                 325                 330 act gtg aaa cat cga aaa cag cag gtg ctt gaa acc gta gct ggc aag     1059
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa     1107
Arg Ser Tyr Arg Leu Ser Met Lys Val Lys Ala Phe Pro Ser Pro Glu
                355                 360                 365
```

-continued

| | | |
|---|---|---|
| gtt gta tgg tta aaa gat ggg tta cct gcg act gag aaa tct gct cgc<br>Val Val Trp Leu Lys Asp Gly Leu Pro Ala Thr Glu Lys Ser Ala Arg<br>370                             375                        380 | | 1155 |
| tat ttg act cgt ggc tac tcg tta att atc aag gac gta act gaa gag<br>Tyr Leu Thr Arg Gly Tyr Ser Leu Ile Ile Lys Asp Val Thr Glu Glu<br>      385                         390                        395 | | 1203 |
| gat gca ggg aat tat aca atc ttg ctg agc ata aaa cag tca aat gtg<br>Asp Ala Gly Asn Tyr Thr Ile Leu Leu Ser Ile Lys Gln Ser Asn Val<br>400                             405                        410 | | 1251 |
| ttt aaa aac ctc act gcc act cta att gtc aat gtg aaa ccc cag att<br>Phe Lys Asn Leu Thr Ala Thr Leu Ile Val Asn Val Lys Pro Gln Ile<br>415                           420                        425                        430 | | 1299 |
| tac gaa aag gcc gtg tca tcg ttt cca gac ccg gct ctc tac cca ctg<br>Tyr Glu Lys Ala Val Ser Ser Phe Pro Asp Pro Ala Leu Tyr Pro Leu<br>                       435                        440                        445 | | 1347 |
| ggc agc aga caa atc ctg act tgt acc gca tat ggt atc cct caa cct<br>Gly Ser Arg Gln Ile Leu Thr Cys Thr Ala Tyr Gly Ile Pro Gln Pro<br>                450                        455                        460 | | 1395 |
| aca atc aag tgg ttc tgg cac ccc tgt aac cat aat cat tcc gaa gca<br>Thr Ile Lys Trp Phe Trp His Pro Cys Asn His Asn His Ser Glu Ala<br>465                             470                        475 | | 1443 |
| agg tgt gac ttt tgt tcc aat aat gaa gag tcc ttt atc ctg gat gct<br>Arg Cys Asp Phe Cys Ser Asn Asn Glu Glu Ser Phe Ile Leu Asp Ala<br>      480                         485                        490 | | 1491 |
| gac agc aac atg gga aac aga att gag agc atc act cag cgc atg gca<br>Asp Ser Asn Met Gly Asn Arg Ile Glu Ser Ile Thr Gln Arg Met Ala<br>495                             500                        505                        510 | | 1539 |
| ata ata gaa gga aag aat aag atg gct agc acc ttg gtt gtg gct gac<br>Ile Ile Glu Gly Lys Asn Lys Met Ala Ser Thr Leu Val Val Ala Asp<br>                       515                        520                        525 | | 1587 |
| tct aga att tct gga atc tac att tgc ata gct tcc aat aaa gtt ggg<br>Ser Arg Ile Ser Gly Ile Tyr Ile Cys Ile Ala Ser Asn Lys Val Gly<br>            530                        535                        540 | | 1635 |
| act gtg gga aga aac ata agc ttt tat atc aca gat gtg cca aat ggg<br>Thr Val Gly Arg Asn Ile Ser Phe Tyr Ile Thr Asp Val Pro Asn Gly<br>         545                        550                        555 | | 1683 |
| ttt cat gtt aac ttg gaa aaa atg ccg acg gaa gga gag gac ctg aaa<br>Phe His Val Asn Leu Glu Lys Met Pro Thr Glu Gly Glu Asp Leu Lys<br>560                             565                        570 | | 1731 |
| ctg tct tgc aca gtt aac aag ttc tta tac aga gac gtt act tgg att<br>Leu Ser Cys Thr Val Asn Lys Phe Leu Tyr Arg Asp Val Thr Trp Ile<br>575                             580                        585                        590 | | 1779 |
| tta ctg cgg aca gtt aat aac aga aca atg cac tac agt att agc aag<br>Leu Leu Arg Thr Val Asn Asn Arg Thr Met His Tyr Ser Ile Ser Lys<br>                       595                        600                        605 | | 1827 |
| caa aaa atg gcc atc act aag gag cac tcc atc act ctt aat ctt acc<br>Gln Lys Met Ala Ile Thr Lys Glu His Ser Ile Thr Leu Asn Leu Thr<br>                  610                        615                        620 | | 1875 |
| atc atg aat gtt tcc ctg caa gat tca ggc acc tat gcc tgc aga gcc<br>Ile Met Asn Val Ser Leu Gln Asp Ser Gly Thr Tyr Ala Cys Arg Ala<br>            625                        630                        635 | | 1923 |
| agg aat gta tac aca ggg gaa gaa atc ctc cag aag aaa gaa att aca<br>Arg Asn Val Tyr Thr Gly Glu Glu Ile Leu Gln Lys Lys Glu Ile Thr<br>640                             645                        650 | | 1971 |
| atc aga gat cag gaa gca cca tac ctc ctg cga aac ctc agt gat cac<br>Ile Arg Asp Gln Glu Ala Pro Tyr Leu Leu Arg Asn Leu Ser Asp His<br>655                             660                        665                        670 | | 2019 |
| aca gtg gcc atc agc agt tcc acc act tta gac tgt cat gct aat ggt<br>Thr Val Ala Ile Ser Ser Ser Thr Thr Leu Asp Cys His Ala Asn Gly | | 2067 |

```
                       675                 680                 685
gtc ccc gag cct cag atc act tgg ttt aaa aac aac cac aaa ata caa      2115
Val Pro Glu Pro Gln Ile Thr Trp Phe Lys Asn Asn His Lys Ile Gln
            690                 695                 700 caa gag cct gga att att tta gga cca gga agc agc acg ctg ttt att      2163
Gln Glu Pro Gly Ile Ile Leu Gly Pro Gly Ser Ser Thr Leu Phe Ile
            705                 710                 715 gaa aga gtc aca gaa gag gat gaa ggt gtc tat cac tgc aaa gcc acc      2211
Glu Arg Val Thr Glu Glu Asp Glu Gly Val Tyr His Cys Lys Ala Thr
        720                 725                 730 aac cag aag ggc tct gtg gaa agt tca gca tac ctc act gtt caa gga      2259
Asn Gln Lys Gly Ser Val Glu Ser Ser Ala Tyr Leu Thr Val Gln Gly
735                 740                 745                 750 acc tcg gac aag tct aat ctg gag ctg atc act cta aca tgc acc tgt      2307
Thr Ser Asp Lys Ser Asn Leu Glu Leu Ile Thr Leu Thr Cys Thr Cys
                755                 760                 765 gtg gct gcg act ctc ttc tgg ctc cta tta acc ctc ctt atc taa          2352
Val Ala Ala Thr Leu Phe Trp Leu Leu Leu Thr Leu Leu Ile *
            770                 775                 780

<210> SEQ ID NO 18
<211> LENGTH: 2383
<212> TYPE: DNA
<213> ORGANISM: Homo sapien
<220> FEATURE:
<221> NAME/KEY: CDS
<222> LOCATION: (14)...(2383)

<400> SEQUENCE: 18
ctcgaggtgc agg atg cag agc aag gtg ctg ctg gcc gtc gcc ctg tgg       49
            Met Gln Ser Lys Val Leu Leu Ala Val Ala Leu Trp
              1               5                  10 ctc tgc gtg gag acc cgg gcc gcc tct gtg ggt ttg cct agt gtt tct      97
Leu Cys Val Glu Thr Arg Ala Ala Ser Val Gly Leu Pro Ser Val Ser
            15                  20                  25 ctt gat ctg ccc agg ctc agc ata caa aaa gac ata ctt aca att aag     145
Leu Asp Leu Pro Arg Leu Ser Ile Gln Lys Asp Ile Leu Thr Ile Lys
        30                  35                  40 gct aat aca act ctt caa att act tgc agg gga cag agg gac ttg gac     193
Ala Asn Thr Thr Leu Gln Ile Thr Cys Arg Gly Gln Arg Asp Leu Asp
 45                  50                  55                  60 tgg ctt tgg ccc aat aat cag agt ggc agt gag caa agg gtg gag gtg     241
Trp Leu Trp Pro Asn Asn Gln Ser Gly Ser Glu Gln Arg Val Glu Val
                 65                  70                  75 act gag tgc agc gat ggc ctc ttc tgt aag aca ctc aca att cca aaa     289
Thr Glu Cys Ser Asp Gly Leu Phe Cys Lys Thr Leu Thr Ile Pro Lys
             80                  85                  90 gtg atc gga aat gac act gga gcc tac aag tgc ttc tac cgg gaa act     337
Val Ile Gly Asn Asp Thr Gly Ala Tyr Lys Cys Phe Tyr Arg Glu Thr
         95                 100                 105 gac ttg gcc tcg gtc att tat gtc tat gtt caa gat tac aga tct cca     385
Asp Leu Ala Ser Val Ile Tyr Val Tyr Val Gln Asp Tyr Arg Ser Pro
     110                 115                 120 ttt att gct tct gtt agt gac caa cat gga gtc gtg tac att act gag     433
Phe Ile Ala Ser Val Ser Asp Gln His Gly Val Val Tyr Ile Thr Glu
125                 130                 135                 140 aac aaa aac aaa act gtg gtg att cca tgt ctc ggg tcc att tca aat     481
Asn Lys Asn Lys Thr Val Val Ile Pro Cys Leu Gly Ser Ile Ser Asn
                145                 150                 155 ctc aac gtg tca ctt tgt gca aga tac cca gaa aag aga ttt gtt cct     529
Leu Asn Val Ser Leu Cys Ala Arg Tyr Pro Glu Lys Arg Phe Val Pro
```

-continued

|     |     |     | 160 |     |     |     |     | 165 |     |     |     |     | 170 |     |     |      |
|-----|-----|-----|-----|-----|-----|-----|-----|-----|-----|-----|-----|-----|-----|-----|-----|------|
| gat | ggt | aac | aga | att | tcc | tgg | gac | agc | aag | aag | ggc | ttt | act | att | ccc | 577  |
| Asp | Gly | Asn | Arg | Ile | Ser | Trp | Asp | Ser | Lys | Lys | Gly | Phe | Thr | Ile | Pro |      |
|     |     | 175 |     |     |     |     | 180 |     |     |     |     | 185 |     |     |     |      |
| agc | tac | atg | atc | agc | tat | gct | ggc | atg | gtc | ttc | tgt | gaa | gca | aaa | att | 625  |
| Ser | Tyr | Met | Ile | Ser | Tyr | Ala | Gly | Met | Val | Phe | Cys | Glu | Ala | Lys | Ile |      |
|     | 190 |     |     |     |     | 195 |     |     |     |     | 200 |     |     |     |     |      |
| aat | gat | gaa | agt | tac | cag | tct | att | atg | tac | ata | gtt | gtc | gtt | gta | ggg | 673  |
| Asn | Asp | Glu | Ser | Tyr | Gln | Ser | Ile | Met | Tyr | Ile | Val | Val | Val | Val | Gly |      |
| 205 |     |     |     |     | 210 |     |     |     |     | 215 |     |     |     |     | 220 |      |
| tat | agg | att | tat | gat | gtg | gtt | ctg | agt | ccg | tct | cat | gga | att | gaa | cta | 721  |
| Tyr | Arg | Ile | Tyr | Asp | Val | Val | Leu | Ser | Pro | Ser | His | Gly | Ile | Glu | Leu |      |
|     |     |     |     | 225 |     |     |     |     | 230 |     |     |     |     | 235 |     |      |
| tct | gtt | gga | gaa | aag | ctt | gtc | tta | aat | tgt | aca | gca | aga | act | gaa | cta | 769  |
| Ser | Val | Gly | Glu | Lys | Leu | Val | Leu | Asn | Cys | Thr | Ala | Arg | Thr | Glu | Leu |      |
|     |     |     | 240 |     |     |     |     | 245 |     |     |     |     | 250 |     |     |      |
| aat | gtg | ggg | att | gac | ttc | aac | tgg | gaa | tac | cct | tct | tcg | aag | cat | cag | 817  |
| Asn | Val | Gly | Ile | Asp | Phe | Asn | Trp | Glu | Tyr | Pro | Ser | Ser | Lys | His | Gln |      |
|     |     | 255 |     |     |     |     | 260 |     |     |     |     | 265 |     |     |     |      |
| cat | aag | aaa | ctt | gta | aac | cga | gac | cta | aaa | acc | cag | tct | ggg | agt | gag | 865  |
| His | Lys | Lys | Leu | Val | Asn | Arg | Asp | Leu | Lys | Thr | Gln | Ser | Gly | Ser | Glu |      |
|     | 270 |     |     |     |     | 275 |     |     |     |     | 280 |     |     |     |     |      |
| atg | aag | aaa | ttt | ttg | agc | acc | tta | act | ata | gat | ggt | gta | acc | cgg | agt | 913  |
| Met | Lys | Lys | Phe | Leu | Ser | Thr | Leu | Thr | Ile | Asp | Gly | Val | Thr | Arg | Ser |      |
| 285 |     |     |     |     | 290 |     |     |     |     | 295 |     |     |     |     | 300 |      |
| gac | caa | gga | ttg | tac | acc | tgt | gca | gca | tcc | agt | ggg | ctg | atg | acc | aag | 961  |
| Asp | Gln | Gly | Leu | Tyr | Thr | Cys | Ala | Ala | Ser | Ser | Gly | Leu | Met | Thr | Lys |      |
|     |     |     |     | 305 |     |     |     |     | 310 |     |     |     |     | 315 |     |      |
| aag | aac | agc | aca | ttt | gtc | agg | gtc | cat | gaa | aaa | cct | ttt | gtt | gct | ttt | 1009 |
| Lys | Asn | Ser | Thr | Phe | Val | Arg | Val | His | Glu | Lys | Pro | Phe | Val | Ala | Phe |      |
|     |     |     | 320 |     |     |     |     | 325 |     |     |     |     | 330 |     |     |      |
| gga | agt | ggc | atg | gaa | tct | ctg | gtg | gaa | gcc | acg | gtg | ggg | gag | cgt | gtc | 1057 |
| Gly | Ser | Gly | Met | Glu | Ser | Leu | Val | Glu | Ala | Thr | Val | Gly | Glu | Arg | Val |      |
|     |     | 335 |     |     |     |     | 340 |     |     |     |     | 345 |     |     |     |      |
| aga | atc | cct | gcg | aag | tac | ctt | ggt | tac | cca | ccc | cca | gaa | ata | aaa | tgg | 1105 |
| Arg | Ile | Pro | Ala | Lys | Tyr | Leu | Gly | Tyr | Pro | Pro | Pro | Glu | Ile | Lys | Trp |      |
|     | 350 |     |     |     |     | 355 |     |     |     |     | 360 |     |     |     |     |      |
| tat | aaa | aat | gga | ata | ccc | ctt | gag | tcc | aat | cac | aca | att | aaa | gcg | ggg | 1153 |
| Tyr | Lys | Asn | Gly | Ile | Pro | Leu | Glu | Ser | Asn | His | Thr | Ile | Lys | Ala | Gly |      |
| 365 |     |     |     |     | 370 |     |     |     |     | 375 |     |     |     |     | 380 |      |
| cat | gta | ctg | acg | att | atg | gaa | gtg | agt | gaa | aga | gac | aca | gga | aat | tac | 1201 |
| His | Val | Leu | Thr | Ile | Met | Glu | Val | Ser | Glu | Arg | Asp | Thr | Gly | Asn | Tyr |      |
|     |     |     |     | 385 |     |     |     |     | 390 |     |     |     |     | 395 |     |      |
| act | gtc | atc | ctt | acc | aat | ccc | att | tca | aag | gag | aag | cag | agc | cat | gtg | 1249 |
| Thr | Val | Ile | Leu | Thr | Asn | Pro | Ile | Ser | Lys | Glu | Lys | Gln | Ser | His | Val |      |
|     |     |     | 400 |     |     |     |     | 405 |     |     |     |     | 410 |     |     |      |
| gtc | tct | ctg | gtt | gtg | tat | gtc | cca | ccc | cag | att | ggt | gag | aaa | tct | cta | 1297 |
| Val | Ser | Leu | Val | Val | Tyr | Val | Pro | Pro | Gln | Ile | Gly | Glu | Lys | Ser | Leu |      |
|     |     | 415 |     |     |     |     | 420 |     |     |     |     | 425 |     |     |     |      |
| atc | tct | cct | gtg | gat | tcc | tac | cag | tac | ggc | acc | act | caa | acg | ctg | aca | 1345 |
| Ile | Ser | Pro | Val | Asp | Ser | Tyr | Gln | Tyr | Gly | Thr | Thr | Gln | Thr | Leu | Thr |      |
|     | 430 |     |     |     |     | 435 |     |     |     |     | 440 |     |     |     |     |      |
| tgt | acg | gtc | tat | gcc | att | cct | ccc | ccg | cat | cac | atc | cac | tgg | tat | tgg | 1393 |
| Cys | Thr | Val | Tyr | Ala | Ile | Pro | Pro | Pro | His | His | Ile | His | Trp | Tyr | Trp |      |
| 445 |     |     |     |     | 450 |     |     |     |     | 455 |     |     |     |     | 460 |      |
| cag | ttg | gag | gaa | gag | tgc | gcc | aac | gag | ccc | agc | caa | gct | gtc | tca | gtg | 1441 |
| Gln | Leu | Glu | Glu | Glu | Cys | Ala | Asn | Glu | Pro | Ser | Gln | Ala | Val | Ser | Val |      |
|     |     |     |     | 465 |     |     |     |     | 470 |     |     |     |     | 475 |     |      |
| aca | aac | cca | tac | cct | tgt | gaa | gaa | tgg | aga | agt | gtg | gag | gac | ttc | cag | 1489 |

```
                Thr Asn Pro Tyr Pro Cys Glu Glu Trp Arg Ser Val Glu Asp Phe Gln
                            480                 485                 490 gga gga aat aaa att gcc gtt aat aaa aat caa ttt gct cta att gaa        1537
Gly Gly Asn Lys Ile Ala Val Asn Lys Asn Gln Phe Ala Leu Ile Glu
            495                 500                 505 gga aaa aac aaa act gta agt acc ctt gtt atc caa gcg gca aat gtg        1585
Gly Lys Asn Lys Thr Val Ser Thr Leu Val Ile Gln Ala Ala Asn Val
            510                 515                 520 tca gct ttg tac aaa tgt gaa gcg gtc aac aaa gtc ggg aga gga gag        1633
Ser Ala Leu Tyr Lys Cys Glu Ala Val Asn Lys Val Gly Arg Gly Glu
525                 530                 535                 540 agg gtg atc tcc ttc cac gtg acc agg ggt cct gaa att act ttg caa        1681
Arg Val Ile Ser Phe His Val Thr Arg Gly Pro Glu Ile Thr Leu Gln
                545                 550                 555 cct gac atg cag ccc act gag cag gag agc gtg tct ttg tgg tgc act        1729
Pro Asp Met Gln Pro Thr Glu Gln Glu Ser Val Ser Leu Trp Cys Thr
            560                 565                 570 gca gac aga tct acg ttt gag aac ctc aca tgg tac aag ctt ggc cca        1777
Ala Asp Arg Ser Thr Phe Glu Asn Leu Thr Trp Tyr Lys Leu Gly Pro
            575                 580                 585 cag cct ctg cca atc cat gtg gga gag ttg ccc aca cct gtt tgc aag        1825
Gln Pro Leu Pro Ile His Val Gly Glu Leu Pro Thr Pro Val Cys Lys
            590                 595                 600 aac ttg gat act ctt tgg aaa ttg aat gcc acc atg ttc tct aat agc        1873
Asn Leu Asp Thr Leu Trp Lys Leu Asn Ala Thr Met Phe Ser Asn Ser
605                 610                 615                 620 aca aat gac att ttg atc atg gag ctt aag aat gca tcc ttg cag gac        1921
Thr Asn Asp Ile Leu Ile Met Glu Leu Lys Asn Ala Ser Leu Gln Asp
                625                 630                 635 caa gga gac tat gtc tgc ctt gct caa gac agg aag acc aag aaa aga        1969
Gln Gly Asp Tyr Val Cys Leu Ala Gln Asp Arg Lys Thr Lys Lys Arg
            640                 645                 650 cat tgc gtg gtc agg cag ctc aca gtc cta gag cgt gtg gca ccc acg        2017
His Cys Val Val Arg Gln Leu Thr Val Leu Glu Arg Val Ala Pro Thr
            655                 660                 665 atc aca gga aac ctg gag aat cag acg aca agt att ggg gaa agc atc        2065
Ile Thr Gly Asn Leu Glu Asn Gln Thr Thr Ser Ile Gly Glu Ser Ile
            670                 675                 680 gaa gtc tca tgc acg gca tct ggg aat ccc cct cca cag atc atg tgg        2113
Glu Val Ser Cys Thr Ala Ser Gly Asn Pro Pro Pro Gln Ile Met Trp
685                 690                 695                 700 ttt aaa gat aat gag acc ctt gta gaa gac tca ggc att gta ttg aag        2161
Phe Lys Asp Asn Glu Thr Leu Val Glu Asp Ser Gly Ile Val Leu Lys
                705                 710                 715 gat ggg aac cgg aac ctc act atc cgc aga gtg agg aag gag gac gaa        2209
Asp Gly Asn Arg Asn Leu Thr Ile Arg Arg Val Arg Lys Glu Asp Glu
            720                 725                 730 ggc ctc tac acc tgc cag gca tgc agt gtt ctt ggc tgt gca aaa gtg        2257
Gly Leu Tyr Thr Cys Gln Ala Cys Ser Val Leu Gly Cys Ala Lys Val
            735                 740                 745 gag gca ttt ttc ata ata gaa ggt gcc cag gaa aag acg aac ttg gaa        2305
Glu Ala Phe Phe Ile Ile Glu Gly Ala Gln Glu Lys Thr Asn Leu Glu
            750                 755                 760 atc att att cta gta ggc acg acg gtg att gcc atg ttc ttc tgg cta        2353
Ile Ile Ile Leu Val Gly Thr Thr Val Ile Ala Met Phe Phe Trp Leu
765                 770                 775                 780 ctt ctt gtc atc atc cta ggg acc gtt taa                                2383
Leu Leu Val Ile Ile Leu Gly Thr Val  *
                785
```

INHIBITOR OF VASCULAR ENDOTHELIAL CELL GROWTH FACTOR

RELATED APPLICATIONS

This application is a divisional of application Ser. No. 09/232,773 filed Jan. 15, 1999, now abandoned; which is a divisional of application Ser. No. 08/786,164 filed Jan. 21, 1997, now U.S. Pat. No. 5,861,484; which is a divisional of application Ser. No. 08/232,538, filed Apr. 21, 1994, now U.S. Pat. No. 5,712,380; which is a continuation-in-part of application Ser. No. 08/038,769 filed Mar. 25, 1993, now abandoned.

BACKGROUND OF THE DISCLOSURE

Recently a new class of cell-derived dimeric mitogens with selectivity for vascular endothelial cells has been identified and designated vascular endothelial cell growth factor (VEGF). VEGF has been purified from conditioned growth media of rat glioma cells [Conn et al., (1990), Proc. Natl. Acad. Sci. U.S.A., 87, pp 2628–2632]; and conditioned growth media of bovine pituitary folliculo stellate cells [Ferrara and Henzel, (1989), Biochem. Biophys. Res. Comm., 161, pp. 851–858; Gozpadorowicz et al., (1989), Proc. Natl. Acad. Sci. U.S.A., 86, pp. 7311–7315] and conditioned growth medium from human U937 cells [Connolly, D. T. et al. (1989), Science, 246, pp. 1309–1312]. VEGF is a dimer with an apparent molecular mass of about 46 kDa with each subunit having an apparent molecular mass of about 23 kDa. VEGF has some structural similarities to platelet derived growth factor (PDGF), which is a mitogen for connective tissue cells but not mitogenic for vascular endothelial cells from large vessels.

The membrane-bound tyrosine kinase receptor, known as FLT, was shown to be a VEGF receptor [DeVries, C. et al., (1992), Science, 255, pp.989–991]. The FLT receptor specifically binds VEGF which induces mitogenesis. Another form of the VEGF receptor, designated KDR, is also known to bind VEGF and induce mitogenesis. The partial cDNA sequence and nearly full length protein sequence of KDR is known as well [Terman, B. I. et al., (1991) Oncogene 6, pp. 1677–1683; Terman, B. I. et al., (1992) Biochem. Biophys. Res. Comm. 187, pp. 1579–1586].

Persistent angiogenesis may cause or exacerbate certain diseases such as psoriasis, rheumatoid arthritis, hemangiomas, angiofibromas, diabetic retinopathy and neovascular glaucoma. An inhibitor of VEGF activity would be useful as a treatment for such diseases and other VEGF-induced pathological angiogenesis and vascular permeability conditions, such as tumor vascularization.

SUMMARY OF THE DISCLOSURE

A naturally-occurring FLT messenger RNA (mRNA) was identified and cloned from vascular endothelial cells. This mRNA is shown to encode most of the extracellular, or soluble, portion of the VEGF receptor, FLT. Soluble receptor molecules including forms containing a C-terminal transmembrane region are also recombinantly engineered for this and other VEGF receptors. These soluble receptors, comprising truncated and modified forms are expressed in recombinant host cells and have VEGF binding properties. The soluble receptor proteins are useful as inhibitors of VEGF activity since they will bind available VEGF preventing it from activating its functional receptors on vascular endothelial cells and could form non-functional heterodimers with full-length membrane anchored VEGF receptors.

BRIEF DESCRIPTION OF THE DRAWINGS

FIG. 2—The DNA sequence of the sVEGF-RI soluble VEGF receptor/VEGF inhibitor is shown.

FIG. 3—The amino acid sequence of the sVEGF-RI soluble VEGF receptor/VEGF inhibitor is shown.

FIG. 5—A 12.5% polyacrylamide electrophoretic gel is shown which demonstrates the high degree of purity obtained for sVEGF-RI.

FIGS. 7A and 7B—Analysis of VEGF binding to sVEGF-RI (A) and corresponding Scatchard plot (B).

FIG. 10—The nucleotide sequence encoding sVEGF-RII is shown.

FIG. 11—The amino acid sequence for sVEGF-RII is shown.

FIG. 12—The nucleotide sequence encoding VEGF-RTMII is shown.

FIG. 13—The amino acid sequence for sVEGF-RTMII is shown.

FIG. 14—The nucleotide sequence encoding sVEGF-RTMI is shown.

FIG. 15—The amino acid sequence for sVEGF-RTMI is shown.

DETAILED DESCRIPTION OF THE DISCLOSURE

The present invention relates to cDNA encoding a soluble VEGF receptor protein (sVEGF-R) which is isolated from VEGF receptor producing cells or is recombinantly engineered from VEGF receptor-encoding DNA. sVEGF-R, as used herein, refers to a protein which can specifically bind to a vascular endothelial cell growth factor without stimulating mitogenesis of vascular endothelial cells.

The amino acid sequence of FLT is known, [Shibuya, M. et al., (1990), Oncogene, 5, pp.519–524] and corresponds to the full length cell-associated VEGF tyrosine kinase receptor. Other VEGF receptors are known to exist. Other known VEGF receptors include, but are not limited to KDR [Terman (1991), supra., and Ternan (1992), supra.]. Mammalian cells capable of producing FLT, KDR and other VEGF receptors include, but are not limited to, vascular endothelial cells. Mammalian cell lines which produce FLT or KDR and other VEGF receptors include, but are not limited to, human endothelial cells. The preferred cells for the present invention include human umbilical vein endothelial cells (HUVEC).

Other cells and cell lines may also be suitable for use to isolate sVEGF-R cDNA. Selection of suitable cells may be done by screening for sVEGF-R binding activity on cell surfaces, in cell extracts or conditioned medium or by screening for gene expression by PCR or hybridization. Methods for detecting soluble receptor activity are well known in the art [Duan, D-S. R. et al., (1991) J.Biol.Chem., 266, pp.413–418] and measure the binding of labelled VEGF. Cells which possess VEGF binding activity in this assay may be suitable for the isolation of sVEGF-R cDNA.

Figure 1:
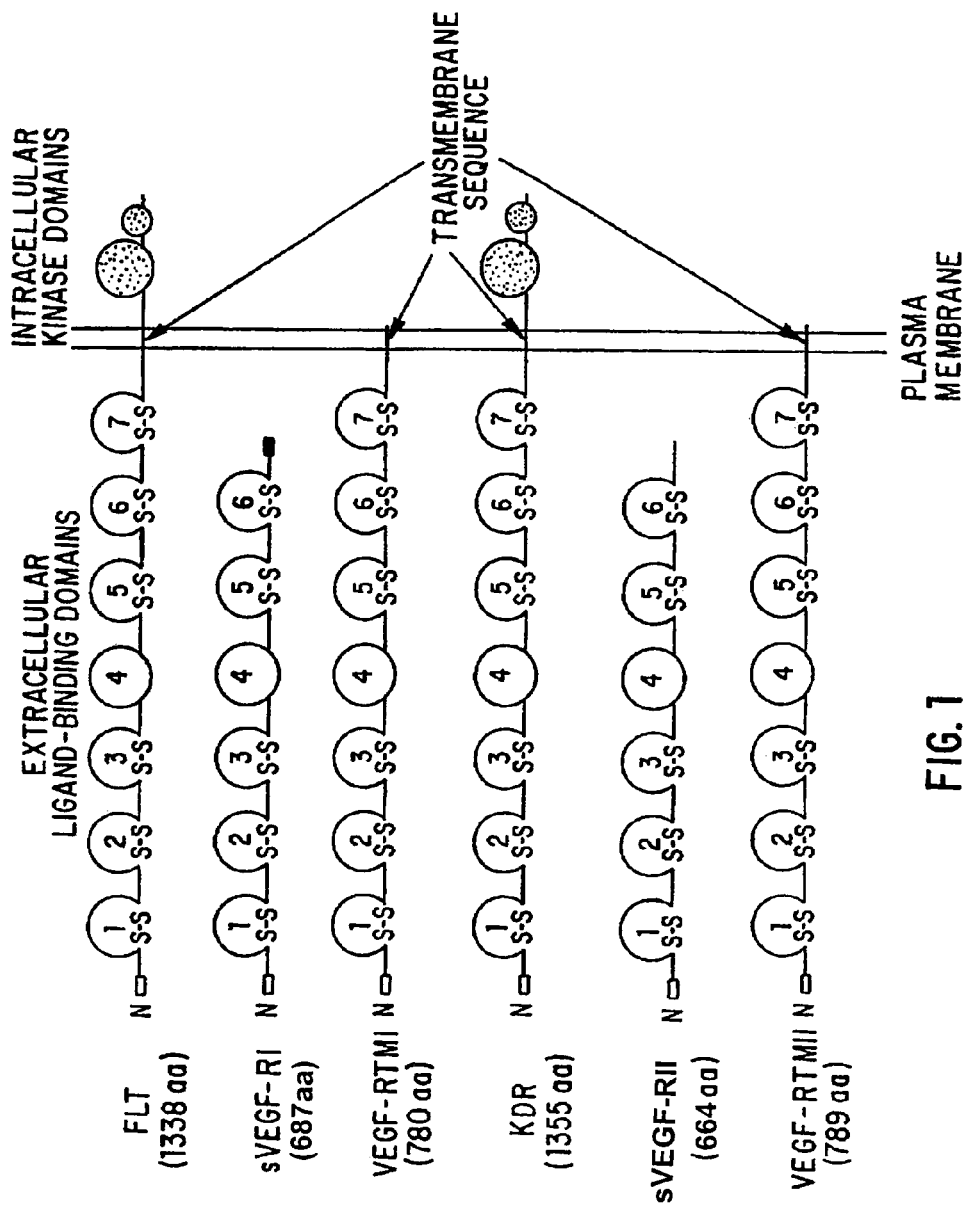
FIG. 1—A schematic diagram of full length VEGF receptors (FLT and KDR), the soluble VEGF receptors (sVEGF-RI and sVEGF-RII) and the soluble receptors containing the C-terminal transmembrane region (VEGF-RTMI and VEGF-RTMII) are shown with the protein domains of each.

Full length FLT producing cells such as human HUVEC cells (American Type Culture Collection, ATCC CRL 1730) [Hoshi, H. and McKeehan, W. L., Proc. Natl. Acad. Sci. U.S.A., (1984) 81, pp. 6413–6417] are grown according to the recommended culture conditions of the ATCC. Full length FLT, and KDR VEGF receptors as well as extracellular region (sVEGF-RI and sVEGF-RII) and extracellular region plus transmembrane region forms (VEGF-RTMI and VEGF-RTMII) are shown in FIG. 1. The full length receptor has an extracellular ligand binding region composed of about seven immunoglobulin-like domains, a membrane spanning sequence (transmembrane domain) and intracellular tyrosine kinase domains. The inhibitory forms of this receptor, which are the subject of the present invention, are also shown in FIG. 1 and lack the intracellular kinase domains, and for some inhibitors, the transmembrane sequence and the C-terminal most Ig-like extracellular domain.

Any of a variety of procedures may be used to molecularly clone sVEGF-R cDNA. These methods include, but are not limited to, direct functional expression of the sVEGF-R gene following the construction of an sVEGF-R-containing cDNA library in an appropriate expression vector system.

Another method is to screen a sVEGF-R-containing cDNA library constructed in a bacteriophage or plasmid shuttle vector with a labelled oligonucleotide probe designed from the predicted amino acid sequence of sVEGF-R. The preferred method consists of screening a sVEGF-R-containing cDNA library constructed in a bacteriophage or plasmid shuttle vector with a partial cDNA encoding at least part of the full length FLT protein. This partial cDNA is obtained by the specific PCR amplification of sVEGF-R DNA fragments through the design of oligonucleotide primers from the known sequence of the full length FLT-encoding DNA.

It is readily apparent to those skilled in the art that other types of libraries, as well as libraries constructed from other cells or cell types, may be useful for isolating sVEGF-R-encoding DNA. Other types of libraries include, but are not limited to, cDNA libraries derived from other cells or cell lines other than HUVECs and genomic DNA libraries.

It is readily apparent to those skilled in the art that suitable cDNA libraries may be prepared from cells or cell lines which have sVEGF-R activity. The selection of cells or cell lines for use in preparing a cDNA library to isolate sVEGF-R cDNA may be done by first measuring secreted sVEGF-R activity using the VEGF binding assay described fully herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding sVEGF-R may also be isolated from a suitable genomic DNA library. Construction of genomic DNA libraries can be performed by standard techniques well known in the art. Well known genomic DNA library construction techiques can be found in Maniatis, T., Fritsch, E. F., Sambrook, J. in Molecular Cloning: A Laboratory Manuel (Cold Spring Harbor Laboratory, Cold Spring Harbor, N.Y., 1982).

Another means of obtaining sVEGF-R molecules is to recombinantly engineer them from DNA encoding the partial or complete amino acid sequence of a VEGF receptor. Examples of other VEGF receptors include, but are not limited to, KDR. Using recombinant DNA techniques, DNA molecules are constructed which encode at least a portion of the VEGF receptor capable of binding VEGF without stimulating mitogenesis. Standard recombinant DNA techniques are used such as those found in Maniatis, et al., supra.

Using one of the preferred methods of the present invention, cDNA clones encoding sVEGF-R are isolated in a two-stage approach employing polymerase chain reaction (PCR) based technology and cDNA library screening. In the first stage, DNA oligonucleotides derived from the extracellular domain sequence information from the known full length FLT, KDR or other VEGF receptor is used to design degenerate oligonucleotide primers for the amplification of sVEGF-R-specific DNA fragments. In the second stage, these fragments are cloned to serve as probes for the isolation of complete sVEGF-R cDNA from a commercially available lambda gt10 cDNA library (Clontech) derived from HUVEC cells (ATCC CRL 1730).

These PCR derived products were used as hybridization probes for screening a lambda gt10 cDNA library derived from HUVECs (Clontech). Plating and plaque lifts of the library were performed by standard methods (T. Maniatis, E. F. Fritsch, J. Sambrook, Molecular Cloning: A Laboratory Manual (Cold Spring Harbor Laboratory, Cold Spring Harbor, N.Y., 1982). The probes were random-primed labelled with $^{32}$P-dCTP to high specific activity and a separate screening of the library ($1\times10^6$ plaques per screen) was conducted with each probe. The probes were added to hybridization buffer (50% formamide, 5× Denhardts, 6×SSC (1×SSC=0.15 M NaCl, 0.015 M Na$_3$citrate.2H$_2$O, pH 7.0), 0.1% SDS, 100 mg/ml salmon sperm DNA) at $1\times10^6$ cpm/ml.

Four positively hybridizing phage were detected using the flt-specific probe. These positively hybridizing phage were observed to be less than full length flt.

Two flt cDNA clones of about 2.0 kb and 2.7 kb in length were subcloned into pGEM vectors (Promega) and bi-directionally sequenced in their entirety by the chain termination method (Sanger et al., (1977) P.N.A.S. USA, 74, pp. 5463–5467,) and shown to contain a single open reading frame of about 569 amino acids. Sequence analysis demonstrated that a portion of the 5' flt coding region was missing from these clones. The remainder of the 5' end was cloned using PCR and combined with the DNA of the clones lacking the 5' end to yield a single open reading frame encoding about 687 amino acids.

The sequence for the cDNA encoding flt-derived sVEGF-RI is shown in Table 1, and was identified in clones 7 and 11. The deduced amino acid sequence of sVEGF-RI from the cloned cDNA is shown in Table 2. Inspection of the deduced amino acid sequence reveals the presence of a single, large open reading frame of 687 amino acids. By comparison with amino acid sequence of the full length FLT VEGF receptor, 31 amino acids are encoded at the C-terminal end of the cDNA which are different from those of FLT.

Using another of the preferred methods of the present invention, DNA encoding sVEGF-R is constructed from a DNA sequence encoding a VEGF receptor. For purposes of illustration, DNA encoding the VEGF receptor known as KDR was utilized. Using the receptor DNA sequence, a DNA molecule is constructed which encodes the extracellular domain of the receptor, or the VEGF binding domain only and is denoted sVEGF-RII. Restriction endonuclease cleavage sites are identified within the receptor DNA and can be utilized directly to excise the extracellular-encoding portion. In addition, PCR techniques as described above may be utilized to produce the desired portion of DNA. It is readily apparent to those skilled in the art that other techniques, which are standard in the art, may be utilized to produce sVEGF-R molecules in a manner analagous to those described above. Such techniques are found, for example, in Maniatis et al., supra.

Additional truncated forms of the VEGF receptor are constructed which contain the transmembrane region. Retention of the transmembrane may facilitate orientation of the inhibitor molecule at the target cell surface. Examples of transmembrane region containing inhibitor molecules include but are not limited to those shown in FIG. 1. VEGF-RTMI and VEGF-RTMII, as shown in FIG. 1, are FLT-related and KDR-related, respectively, transmembrane region containing receptor inhibitors. Construction of transmembrane region containing molecules, such as VEGF-RTMI and VEGF-RTMII, is done by standard techniques known in the art including but not limited to utilizing convenient restriction endonuclease cleavage sites or PCR techniques as described herein. It is readily understood by those skilled in the art that various forms of the inhibitors of a VEGF receptor, as disclosed herein, containing only the extracellular region or containing, in addition, the transmembrane region may be constructed which have substantially the same activity.

The cloned sVEGF-R cDNA obtained through the methods described above may be recombinantly expressed by molecular cloning into an expression vector containing a suitable promoter and other appropriate transcription regulatory elements, and transferred into prokaryotic or eukaryotic host cells to produce recombinant sVEGF-R. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, fungal cells, yeast cells, plant cells, insect cells and animal cells.

Specifically designed vectors allow the shuttling of DNA between hosts such as bacteria-yeast or bacteria-animal or bacteria-insect cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant sVEGF-R in mammalian cells. Commercially available mammalian expression vectors which may be suitable for recombinant sVEGF-R expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMT-neo(342-12) (ATCC 37224), pRSVgpt (ATCC 37199), pRS-Vneo (ATCC 37198), pSV2-dhfr (ATCC 37146), pUCTag (ATCC 37460), and gZD35 (ATCC 37565).

DNA encoding sVEGF-R may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila, moth, mosquito and armyworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171). Insect cell lines which may be suitable and are commercially available include but are not limited to 3M-S (ATCC CRL 8851) moth (ATCC CCL 80) mosquito (ATCC CCL 194 and 195; ATCC CRL 1660 and 1591) and armyworm (Sf9, ATCC CRL 1711).

The expression vector may be introduced into host cells via any one of a number of techniques including but not limited to transformation, transfection, liposome or protoplast fusion, and electroporation. The expression vector-containing cells are clonally propagated and individually analyzed to determine whether they produce sVEGF-R protein. Identification of sVEGF-R expressing host cell clones may be done by several means, including but not limited to immunological reactivity with anti-sVEGF-R antibodies, binding to radiolabelled VEGF, and the presence of host cell-secreted sVEGF-R activity.

Expression of sVEGF-R DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Levels of sVEGF-R protein produced by host cells may be quantitated by immunoaffinity and/or ligand affinity techniques. sVEGF-R-specific affinity beads or sVEGF-R-specific antibodies are used to isolate $^{35}$S-methionine labelled or unlabelled sVEGF-R protein. Labelled sVEGF-R protein is analyzed by SDS-PAGE. Unlabelled sVEGF-R protein is detected by Western blotting, ELISA or RIA assays employing sVEGF-R specific antibodies, or by ligand blotting with labelled VEGF.

Following expression of sVEGF-R in a recombinant host cell, sVEGF-R protein may be recovered to provide sVEGF-R in active form, capable of binding VEGF without stimulating mitogenesis. Several sVEGF-R purification procedures are available and suitable for use. sVEGF-R may be purified from cell lysates and extracts, or from conditioned culture medium, by various combinations of, or individual application of salt fractionation, ion exchange chromatography, size exclusion chromatography, hydroxylapatite adsorption chromatography, reversed phase chromatography, heparin sepharose chromatography, VEGF ligand affinity chromatography, and hydrophobic interaction chromatography.

In addition, recombinant sVEGF-R can be separated from other cellular proteins by use of an immuno-affinity column made with monoclonal or polyclonal antibodies specific for full length sVEGF-R, or polypeptide fragments of sVEGF-R.

Identification of sVEGF-RI—In an attempt to clone the VEGF receptor cDNA (flt) a HUVEC lgt10 cDNA library was screened with a DNA probe derived from the extracellular domain of the membrane bound or full length form of this receptor as shown in FIG. 1. Four incomplete clones, all lacking various lengths of 5' coding sequence, were isolated from screening a total of $1 \times 10^6$ plaques. Two of these isolates represent partial clones that were identical to full length flt, one of which contained the complete 3' coding region of the form described by Shibuya et al., supra. The other two clones were identical to full length flt up to base pair number 2219 (Table 1 and FIG. 2) where they then diverged from full length flt. These clones (clone 7 and 11) coded for an additional unique 31 amino acids before the open reading frame is terminated by a TAA codon (Table 2 and FIG. 3).

Clone 7 and 11 coded for a protein with a predicted molecular mass of about 75 kDa containing 12 putative N-linked glycosylation sites. This version of the receptor was missing the transmembrane and intracellular kinase domains and thus coded for a natural soluble form of the VEGF receptor (sVEGF-RI). Further, the protein molecule predicted by sVEGF-RI has only the first six Ig-like domains, missing the one closest to the transmembrane sequence (FIG. 1). The 31 amino acids at the C-terminal end of sVEGF-RI contain two cysteine residues, but does not resemble an Ig domain.

Expression of sVEGF-RI in Sf9 cells—To analyze the binding and biological properties of this form of the receptor, the protein was expressed using a baculovirus expression system. Clone 7 was missing about 350 base pairs of coding sequence at the 5' end. This region was cloned by PCR using the primers described above and in Example 1. A clone containing the complete coding region of sVEGF-RI was constructed by combining the 5' PCR fragment with sVEGF-RI clone 7 which overlapped at a SacI site. The 5' EcoRI site was then changed to a BamHI site and the full length sVEGF-RI was cloned into pBluebac III (Invitrogen) as a BamHI/BamHI fragment. A recombinant baculovirus P-3 stock containing the sVEGF-RI gene 3' in relation to the polyhedrin promoter was then prepared as described herein.

Figure 4:
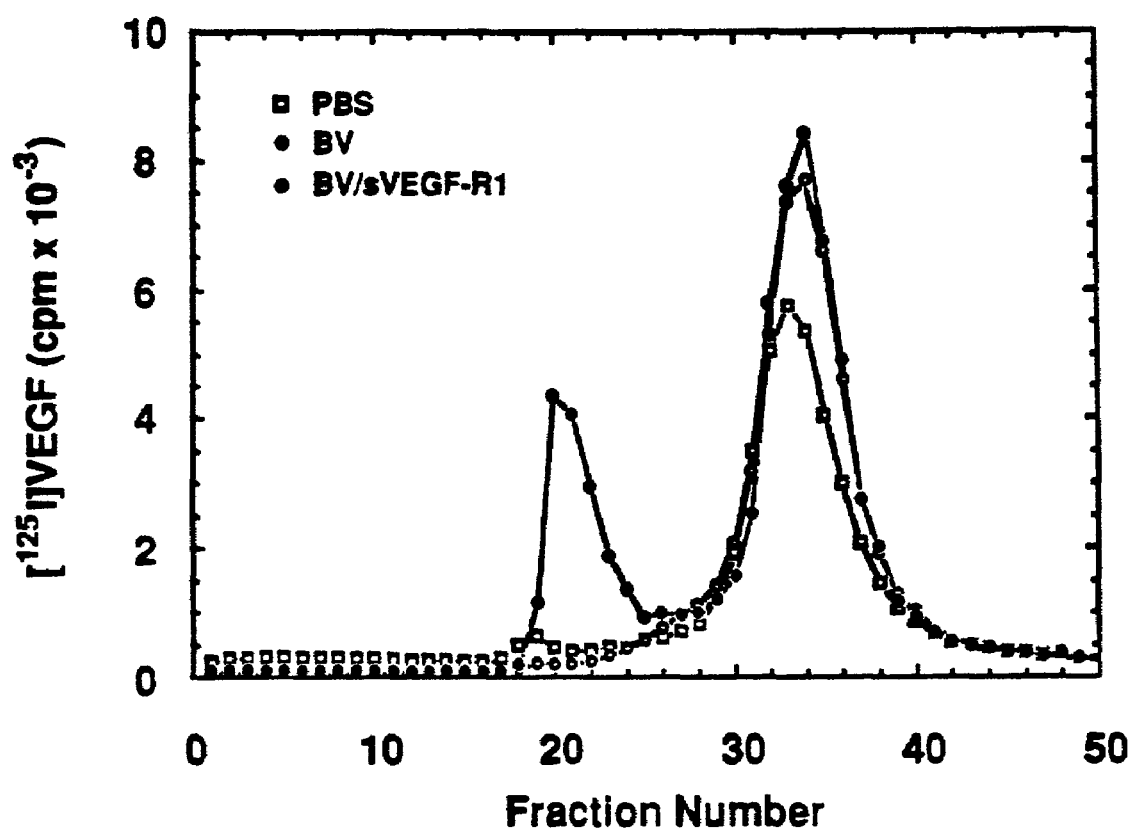
FIG. 4—Demonstration that recombinant host cells express sVEGF-RI is shown by the formation of high molecular weight complexes of sVEGF-RI and [$^{125}$I]VEGF and separated by size exclusion chromatography.

Culture media from small scale infections were tested for the ability to form high molecular weight complexes with [$^{125}$I]VEGF. The labeled ligand and culture media from the baculovirus infected cells were combined and incubated. The reactions were then analyzed by size exclusion chromatography. When the wild-type infected culture medium was mixed with the radioactive ligand (FIG. 4) a single radioactive peak was observed. However, when the sVEGF-RI infected culture medium was used, a high molecular weight complex was formed, as evident by the appearance of a second peak in this reaction eluting near the void volume of the column. This experiment showed that the natural soluble form of the FLT VEGF receptor, sVEGF-RI, forms a high molecular weight complex with VEGF.

The recombinantly produced sVEGF-R is purified from the recombinant host cell extracts or cell culture fluid using heparin-sepharose column chromatography which specifically binds the sVEGF-R protein. The heparin-sepharose bound VEGF-R column is washed using a suitable buffer containing between b 0.1M and 0.6M NaCl which removes contaminating proteins without significant loss of sVEGF-R. The sVEGF-R is eluted from the heparin-sepharose column using a suitable buffer containing about 1M NaCl, yielding substantially purified sVEGF-R.

Binding of the sVEGF-RI to VEGF—The binding of $^{125}$I-labelled VEGF to sVEGF-RI was characterized by crosslinking, and by complex formation with sVEGF-RI absorbed to 96 well plates.

Figure 6:
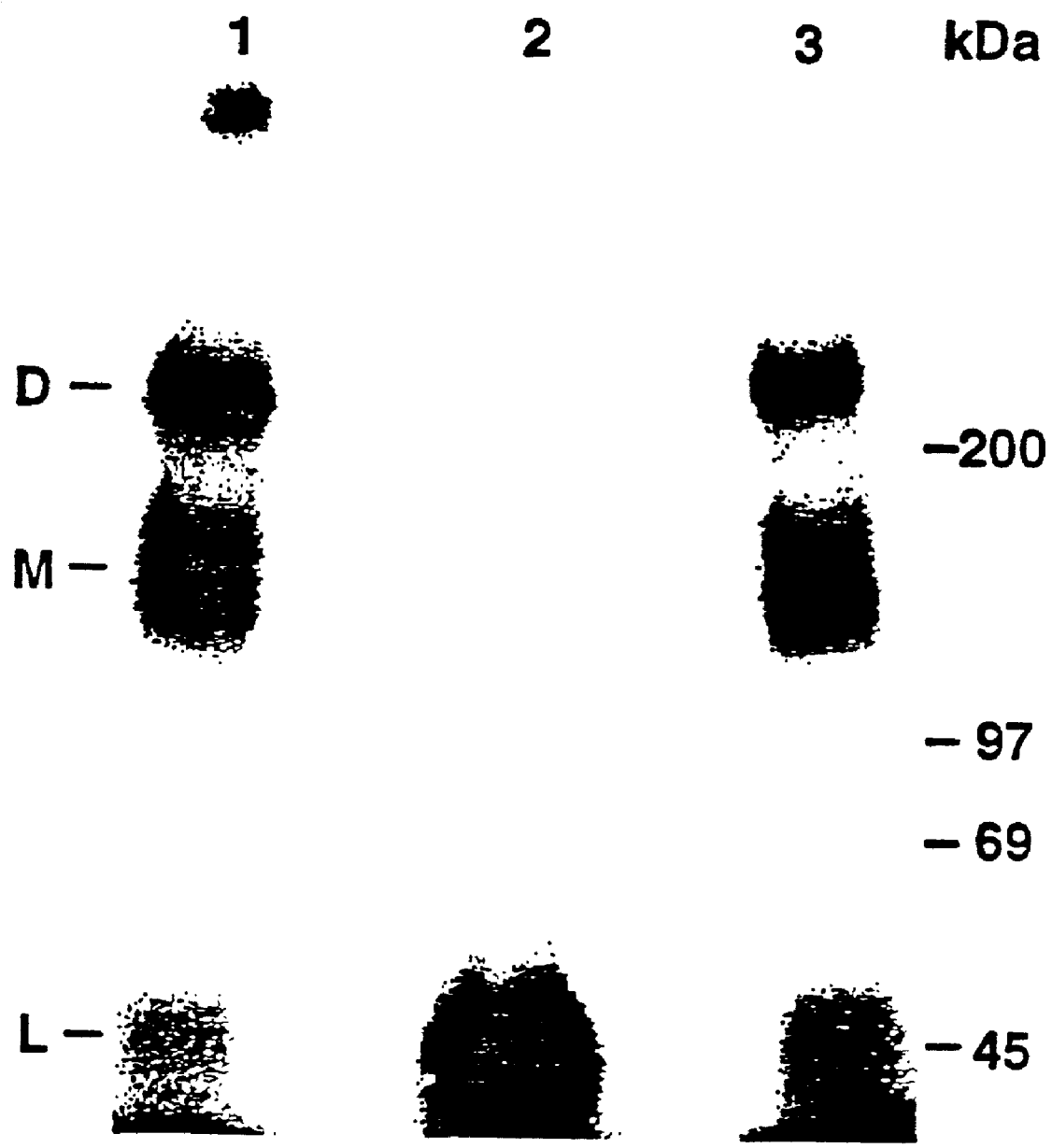
FIG. 6—Cross-linked products of sVEGF-RI and [$^{125}$I] VEGF are shown at about 145 kDa, and at about 245 kDa.

The crosslinked products are shown in FIG. 6. The sVEGF-RI was cross-linked to [$^{125}$I]VEGF (lane 1); in the presence of unlabelled VEGF (lane 2) and unlabelled bFGF (lane 3). Two high molecular weight bands (about 145 kDa and 245 kDa) were formed in the sVEGF-RI and [$^{125}$I] VEGF containing reaction, and in the sVEGF-RI and [$^{125}$I] VEGF plus an excess of unlabelled bFGF reaction. The two high molecular weight bands were not present when sVEGF-RI was incubated with [$^{125}$I]VEGF plus an excess of unlabelled VEGF, demonstrating the specificity of sVEGF-RI for VEGF, and the ability of sVEGF-RI to form a dimer. The 145 kDa band is presumably a crosslinked complex containing one receptor molecule (about 100 kDa) and a VEGF dimer (about 46 kDa). As shown in FIG. 6 complexes containing two receptor molecules (about 245 kDA) were also observed. This suggests that each VEGF dimer can bind one or two receptor molecules and that the soluble form of the VEGF receptor may undergo ligand-induced dimerization.

The affinity of sVEGF-RI for VEGF was evaluated by absorbing sVEGF-RI to the surface of a 96 well plate, followed by blocking the nonspecific sites with 0.5% gelatin. Variable amounts of labeled ligand were added to each well. These results demonstrate that sVEGF-RI binds VEGF with high affinity with an apparent $K_d$ of about 20 pM (FIG. 7). Since the soluble form of the receptor is missing the Ig domain closest to the transmembrane spanning region, this domain is not required for ligand binding.

The sVEGF-RI is shown to inhibit binding of VEGF to HUVECs by incubating cultured HUVECs with [$^{125}$I]VEGF and various amounts of sVEGF-RI. Following incubation, the cells are washed to remove unbound [$^{125}$I]VEGF. The cells are then solubilized and the amount of cell-associated $^{125}$I is determined by gamma counter, which demonstrates the amount of [$^{125}$I]VEGF which was capable of binding to the cellular VEGF receptor in the presence of sVEGF-RI. Using this method, it is demonstrated that sVEGF-RI was capable of inhibiting [$^{125}$I]VEGF binding to HUVECs VEGF receptor (see FIG. 8).

Figure 9:
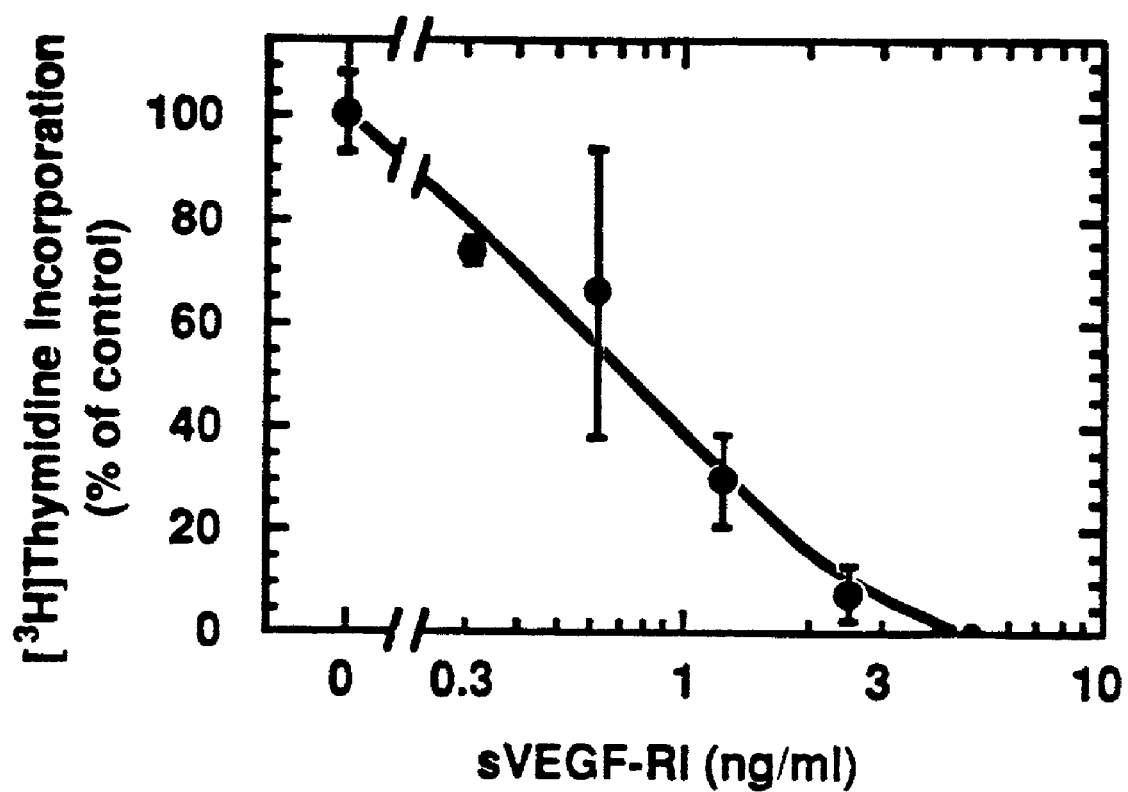
FIG. 9—Inhibition of VEGF-mediated mitogenesis on HUVECs is shown using sVEGF-RI.

Since sVEGF-RI was able to inhibit VEGF binding to cell receptors, it was then determined that sVEGF-RI could inhibit VEGF induced mitogenesis. Cells are preincubated with sVEGF-RI and then incubated with VEGF in the presence of [$^3$H]thymidine. Following incubation, the amount of cellular DNA-incorporated [$^3$H]thymidine is measured which indicates whether VEGF has induced mitogenesis and caused [$^3$H]thymidine to be incorporated into cellular DNA. The presence of sVEGF-RI inhibits the ability of VEGF to stimulate mitogenesis as shown in FIG. 9.

The inhibitor of the present invention can be used for the inhibition of VEGF activity. The inhibitor can be used either topically or intravascularly. For topical applications the formulation would be applied directly at a rate of about 10 ng to about 1 mg/cm$^2$/day. For intravaneous applications, the inhibitor is used at a rate of about 1 mg to about 10 mg/kg/day of body weight. For internal use, the formulation may be released directly into the region to be treated either from implanted slow release polymeric material or from slow release pumps or repeated injections. The release rate in either case is about 100 ng to about 100 mg/day/cm$^3$.

For non-topical application the VEGF inhibitor is administered in combination with pharmaceutically acceptable carriers or diluents such as phosphate buffer, saline, phosphate buffered saline, Ringer's solution, and the like, in a pharmaceutical composition, according to standard pharmaceutical practice. For topical application, various pharmaceutical formulations are useful for the administration of the active compound of this invention. Such formulations include, but are not limited to, the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxy alkyl celluloses and alkylhydroxyalkyl celluloses, for example methylcellulose, hydroxyethyl cellulose, carboxymethyl cellulose, hydroxypropyl methylcellulose, and hydroxypropyl cellulose; polyoxamers such as Pluronic® Polyols exemplified by Pluronic® F-127; tetronics such as tetronic 1508; and alginates such as sodium alginate.

The following examples are provided as illustrative of the present invention without, however, limiting the same thereto.

EXAMPLE 1

Cloning flt-related sVEGF-RI—A 580 base pair DNA probe for flt was obtained by PCR of the HUVEC phage library using the primers 5' GCACCTTGGTTGTGGCTGAC 3' (SEQ. ID. No.: 1) and 5' TGGAATTCGTGCTGCTTCCTG-GTCC 3'(SEQ. ID. No.: 2). The resulting DNA fragment was cloned into pGEM3Z as a XbaI/EcoRI fragment. The probe was prepared by the random priming method [Feinberg, A. P. and Vogelstein, B., (1983) Anal.Biochem., 132, pp.6–13] using the megaprime kit (Amersham) at a specific activity of 1×10$^7$ cpm/ng. The HUVEC cDNA library was plated at a density of 5×10$^4$ plaques/150 cm plate then about 1×10$^6$ plaques were screened by hybridization as previously described [Maniatis, T. et al., supra]. Briefly, following prehybridization at 42° C. for 2 hours in 50% formamide, 5×SSC, 5× Denhardt's solution, 0.1% SDS, 100 mg/ml salmon sperm DNA (hybridization buffer) the filters were hybridized with the probe for 16 hours at 42° C. in hybridization buffer. The filters were washed one time for 15 min at room temperature in 2× SSC then three times at 55° C. in 0.1×SSC. Four positive plaques were identified and rescreened two additional times to obtain homogeneous isolates. Inserts were cloned into pGEM3Z for DNA sequence analysis. Two of these clones were identified which contained less than the full length flt coding region. DNA sequence analysis showed that these clones lacked the 5' coding region of flt. The DNA sequence is shown in Table 1 and FIG. 2, and the deduced amino acid sequence is shown in Table 2 and FIG. 3. The 5' end of flt was cloned by PCR using the primers 5' GGAATTCCGCGCTCACCATGGT-CAGC 3' (SEQ.ID.NO.:3) and 5' TTTGAATTCACCCG-GCAGGGAATGACG 3' (SEQ.ID.NO.:4). The PCR fragment generated with this set of primers was cloned into flt clone 7 as an EcoRI/SacI fragment.

TABLE 1

| | |
|---|---|
| GCGGACACTCCTCTCGGCTCCTCCCCGGCAGCGGCGGCGGCTCG | (SEQ ID NO.:5) |
| GAGCGGGCTCCGGGGCTCGGGTGCAGCGGCCAGCGGGCCTGGC | |
| GGCGAGGATTACCCGGGGAAGTGGTTGTCTCCTGGCTGGAGCC | |
| GCGAGACGGGCGCTCAGGGCGCGGGGCCGGCGGCGGCGAACG | |
| AGAGGACGGACTCTGGCGGCCGGGTCGTTGGCCGGGGAGCGC | |
| GGGCACCGGGCGAGCAGGCCGCGTCGCGCTCACC ATG GTC | |
| AGC TAC TGG GAC ACC GGG GTC CTG CTG TGC GCG CTG | |
| CTC AGC TGT CTG CTT CTC ACA GGA TCT AGT TCA GGT TCA | |
| AAA TTA AAA GAT CCT GAA CTG AGT TTA AAA GGC ACC | |
| CAG CAC ATC ATG CAA GCA GGC CAG ACA CTG CAT CTC | |
| CAA TGC AGG GGG GAA GCA GCC CAT AAA TGG TCT TTG | |
| CCT GAA ATG GTG AGT AAG GAA AGG GAA AGG CTG AGC | |
| ATA ACT AAA TCT GCC TGT GGA AGA AAT GGC AAA CAA | |
| TTC TGC AGT ACT TTA ACC TTG AAC ACA GCT CAA GCA | |
| AAC CAC ACT GGC TTC TAC AGC TGC AAA TAT CTA GCT | |
| GTA CCT ACT TCA AAG AAG AAG GAA AGA GAA TCT GCA | |
| ATC TAT ATA TTT ATT AGT GAT ACA GGT AGA CCT TTC | |
| GTA GAG ATG TAC AGT GAA ATC CCC GAA ATT ATA CAC | |
| ATG ACT GAA GGA AGG GAG CTC GTC ATT CCC TGC CGG | |

TABLE 1-continued

```
GTT ACG TCA CCT AAC ATC ACT GTT ACT TTA AAA AAG
TTT CCA CTT GAC ACT TTG ATC CCT GAT GGA AAA CGC
ATA ATC TGG GAC AGT AGA AAG GGC TTC ATC ATA TCA
AAT GCA ACG TAC AAA GAA ATA GGG CTT GTG ACC TGT
GAA GCA ACA GTC AAT GGG CAT TTG TAT AAG ACA AAC
TAT GTG ACA CAT CGA CAA ACC AAT ACA ATC ATA GAT
GTC CAA ATA AGC ACA CCA CGC CCA GTC AAA TTA CTT
AGA GGC CAT ACT CTT GTC CTC AAT TGT ACT GCT ACC ACT
CCC TTG AAC ACG AGA GTT CAA ATG ACC TGG AGT TAC
CCT GAT GAA AAA AAT AAG AGA GCT TCC GTA AGG CGA
CGAATT GAC CAA AGC AAT TCC CAT GCC AAC ATA TTC TAC
AGT GTT CTTACT ATT GAC AAA ATG CAG GAC AAA GAC
AAA GGA CTT TAT ACT TGTCGT GTA AGG AGT GGA CCA
TCA TTC AAA TCT GTT AAC ACC TCA GTGCAT ATA TAT GAT
AAA GCA TTC ATC ACT GTG AAA CAT CGA AAA CAGCAG
GTG CTT GAA ACC GTA GCT GGC AAG CGG TCT TAC CGG
CTC TCTATG AAA GTG AAG GCA TTT CCC TCG CCG GAA GTT
GTA TGG TTA AAAGAT GGG TTA CCT GCG ACT GAG AAA
TCT GCT CGC TAT TTG ACT CGT GGC TAC TCG TTA ATT ATC
AAG GAC GTA ACT GAA GAG GAT GCA GGG AAT TAT ACA
ATC TTG CTG AGC ATA AAA CAG TCA AAT GTG TTT AAA
AAC CTC ACT GCC ACT CTA ATT GTC AAT GTG AAA CCC
CAG ATT TAC GAA AAG GCC GTG TCA TCG TTT CCA GAC
CCG GCT CTC TAC CCA CTG GGC AGC AGA CAA ATC CTG
ACT TGT ACC GCA TAT GGT ATC CCT CAA CCT ACA ATC
AAG TGG TTC TGG CAC CCC TGT AAC CAT AAT CAT TCC
GAA GCA AGG TGT GAC TTT TGT TCC AAT AAT GAA GAG
TCC TTT ATC CTG GAT GCT GAC AGC AAC ATG GGA AAC
AGA ATT GAG AGC ATC ACT GAG GGG ATG GCA ATA ATA
GAA GGA AAG AAT AAG ATG GCT AGC ACC TTG GTT GTG
GCT GAC TGT AGA ATT TCT GGA ATC TAC ATT TGC ATA
GCT TCC AAT AAA GTT GGG ACT GTG GGA AGA AAC ATA
AGC TTT TAT ATC ACA GAT GTG CCA AAT GGG TTT CAT
GTT AAC TTG GAA AAA ATG CCG ACG GAA GGA GAG GAC
CTG AAA CTG TCT TGC ACA GTT AAC AAG TTC TTA TAC
AGA GAG GTT ACT TGG ATT TTA CTG CGG ACA GTT AAT
AAC AGA ACA ATG CAC TAC AGT ATT AGC AAG CAA AAA
ATG GCC ATC ACT AAG GAG CAC TCC ATC ACT CTT AAT
CTT ACC ATC ATG AAT GTT CCC TGC AAG ATT TCA GGC
```

TABLE 1-continued

```
ACC TAT GCC TGC AGA GCC AGG AAT GTA TAC ACA GGG
GAA GAA ATC CTC CAG AAG AAA GAA ATT ACA ATC AGA
GTT GAG CAC TGC AAC AAA AAG GCT GTT TTC TCT CGG
ATC TCC AAA TTT AAA AGC ACA AGG AAT GAT TGT ACC
ACACAAAGTAATGTAAAACATTAAAGGACTCATTAAAAAGTA
ACAGTTGTCTCATATCATCTTGATTTATTGTCACTGTTGCTAAC
TTTCAGGCTCGGAGGAGATGCTCCTCCCAAAATGAGTTCGGAG
ATGATAGCAGTAATAATGAGACCCCCGGGCTCCAGCTCTGGGC
CCCCCATTCAGGCCGAGGGGGCTGCTCCGGGGGCCGACTTGG
TGCACGTTTGGATTTGGAGGATCCCTGCACTGCCTTCTCTGTGT
TTGTTGCTCTTGCTGTTTTCTCCTGCCTGATAAACAACAACTTG
GGATGATCCTTTCCATTTTGATGCCAACCTCTTTTTATTTTTAA
GCGGCGCCCTATAGT
```

TABLE 2

| | | | | | | | | | | | | | | |
|---|---|---|---|---|---|---|---|---|---|---|---|---|---|---|
Met Val Ser Tyr Trp Asp Thr Gly Val Leu Leu Cys Ala Leu Leu Ser  (SEQ ID NO.:6)
Cys Leu Leu Leu Thr Gly Ser Ser Ser Gly Ser Lys Leu Lys Asp Pro
Glu Leu Ser Leu Lys Gly Thr Gln His Ile Met Gln Ala Gly Gln Thr
Leu His Leu Gln Cys Arg Gly Glu Ala Ala His Lys Trp Ser Leu Pro
Glu Met Val Ser Lys Glu Ser Glu Arg Leu Ser Ile Thr Lys Ser Ala Cys
Gly Arg Asn Gly Lys Gln Phe Cys Ser Thr Leu Thr Len Asn Thr Ala
Gln Ala Asn His Thr Gly Phe Tyr Ser Cys Lys Tyr Len Ala Val Pro
Thr Ser Lys Lys Lys Glu Thr Gln Ser Ala Ile Tyr Ile Phe Ile Ser Asp
Thr Gly Arg Pro Phe Val Gln Met Tyr Ser Glu Ile Pro Gln Ile Ile His
Met Thr Gln Gly Arg Glu Leu Val Ile Pro Cys Arg Val Thr Ser Pro
Asn Ile Thr Val Thr Leu Lys Lys Phe Pro Leu Asp Thr Leu Ile Pro
Asp Gly Lys Arg Ile Ile Trp Asp Ser Arg Lys Gly Phe Ile Ile Ser Asn
Ala Thr Tyr Lys Glu Ile Gly Leu Leu Thr Cys Gln Ala Thr Val Asn
Gly His Leu Tyr Lys Thr Asn Tyr Leu Thr His Arg Gln Thr Asn Thr
Ile Ile Asp Val Gln Ile Ser Thr Pro Arg Pro Val Lys Leu Leu Arg Gly
His Thr Leu Val Leu Asn Cys Thr Ala Thr Thr Pro Leu Asn Thr Arg
Val Gln Met Thr Trp Ser Tyr Pro Asp Gln Lys Asn Lys Arg Ala Ser
Val Arg Arg Arg Ile Asp Gln Ser Asn Ser His Ala Asn Ile Phe Tyr Ser
Val Leu Thr Ile Asp Lys Met Gln Asn Lys Asp Lys Gly Leu Tyr Thr
Cys Arg Val Arg Ser Gly Pro Ser Phe Lys Ser Val Asn Thr Ser Val His
Ile Tyr Asp Lys Ala Phe Ile Thr Val Lys His Arg Lys Gln Gln Val Leu
Gln Thr Val Ala Gly Lys Arg Ser Tyr Arg Leu Ser Met Lys Val Lys
Ala Phe Pro Ser Pro Glu Val Val Trp Leu Lys Asp Gly Leu Pro Ala
Thr Glu Lys Ser Ala Arg Tyr Leu Thr Arg Gly Tyr Ser Leu Ile Ile Lys

TABLE 2-continued

```
Asp Val Thr Glu Glu Asp Ala Gly Asn Tyr Thr Ile Leu Leu Ser Ile Lys

Gln Ser Asn Val Phe Lys Asn Leu Thr Ala Thr Leu Ile Val Asn Val

Lys Pro Gln Ile Tyr Glu Lys Ala Val Ser Ser Phe Pro Asp Pro Ala Leu

Tyr Pro Leu Gly Ser Arg Gln Ile Leu Thr Cys Thr Ala Tyr Gly Ile Pro

Gln Pro Thr Ile Lys Trp Phe Trp His Pro Cys Asn His Asn His Ser Glu

Ala Arg Cys Asp Phe Cys Ser Asn Asn Glu Glu Ser Phe Ile Leu Asp

Ala Asp Ser Asn Met Gly Asn Arg Ile Glu Ser Ile Thr Gln Arg Met Ala

Ile Ile Glu Gly Lys Asn Lys Met Ala Ser Thr Leu Val Val Ala Asp Ser

Arg Ile Ser Gly Ile Tyr Ile Cys Ile Ala Ser Asn Lys Val Gly Thr Val

Gly Arg Asn Ile Ser Phe Tyr Ile Thr Asp Val Pro Asn Gly Phe His Val

Asn Leu Glu Lys Met Pro Thr Glu Gly Gln Asp Leu Lys Leu Ser Cys

Thr Val Asn Lys Phe Leu Tyr Arg Asp Val Thr Trp Ile Leu Leu Arg

Thr Val Asn Asn Arg Thr Met His Tyr Ser Ile Ser Lys Gln Lys Met

Ala Ile Thr Lys Glu His Ser Ile Thr Leu Asn Leu Thr Ile Met Asn Val

Ser Leu Gln Asp Ser Gly Thr Tyr Ala Cys Arg Ala Arg Asn Val Tyr

Thr Gly Glu Glu Ile Leu Gln Lys Lys Glu Ile Thr Ile Arg Gly Glu His

Cys Asn Lys Lys Ala Val Phe Ser Arg Ile Ser Lys Phe Lys Ser Thr Arg

Asn Asp Cys Thr Thr Gln Ser Asn Val Lys His . . .
```

EXAMPLE 2

Expression of sVEGF-RI in Sf9 insect cells—The full length sequence encoding sVEGF-RI was cloned as an EcoRI/BamHI fragment into pGEM3Z. The EcoRI site was then modified to a BamHI site and cloned into pBlueBac III 3' of the polyhedrin promoter (psFLTblue). This plasmid was transfected into Sf9 armyworm cells using liposomes. After 48 hours the medium from the transfected cells which contains recombinant polyhedrin virus particles, was harvested. Dilutions ($10^{3-104}$ fold) of the virus were prepared and plaque purified in soft agar containing 150 mg/ml 5-bromo-4-chloro-3-indolyl-β-D-galactoside. Recombinant plaques were identified by blue color and used to infect Sf9 cells ($5 \times 10^5$ cells/well) in 12 well plates. Medium (100 ml) from polyhedrin minus infections was used to prepare P-2 viral stocks by infecting $2.5 \times 10^6$ cells in a T-25 flask. Large scale high titer P-3 viral stocks were then prepared by infecting Sf9 cells (500 ml at $2 \times 10^6$ cells/ml) with 5 ml of the P-2 stock then incubating at 27° C. for 5–6 days and the medium was harvested by centrifugation. Protein expression was accomplished by infecting cells at a density of $2-2.5 \times 10^6$ cells/ml with a multiplicity of infection of 5–10. Twenty four hours after infection the cells were changed to a serum free medium (SF900II, Gibco BRL), incubated for an additional 48 hours and the medium was collected. This conditioned medium contains the recombinantly expressed sVEGF-RI protein.

EXAMPLE 3

Iodination of VEGF and PlGF—$^{125}$I-labeled human recombinant VEGF was prepared by the chloramine T method (Hunter, W. M. and Greenwood, F. C., (1962) Nature (London), 194, pp. 495–496). Briefly, 1 mg of VEGF in 30% acetonitrile/0.1% trifluroacetic acid was adjusted to pH 7.1 by the addition of ⅓ volume of 0.4 M sodium phosphate buffer, pH 7.1. Freshly dissolved chloramine T (4 ml of a 2 mg/ml stock in 0.1 M sodium phosphate buffer, pH 7.1) was added to the VEGF solution and reacted for 45 seconds at room temperature (total volume of 150 ml). The reaction was stopped by the addition of 50 ml of 10 mM KI and 50 ml of 2 mg/ml meta bisufite. The labeled ligand was separated from the free $^{125}$I by gel filtration on a 0.7×15 cm Sephadex G-25 column equilibrated in PBS with 1 mg/ml gelatin. Fractions were counted in a Packard g counter, aliquoted and stored at −70° C. VEGF was labeled to a specific activity of $5 \times 10^5$ to $1 \times 10^6$ cpm/ng. Recombinant human PlGF was iodinated by the chloramine-T method as described herein, to specific activity between approximately $3 \times 10^5$-$9 \times 10^5$ cpm/ng. After iodination, PlGF was stored at 4° C. in PBS containing 1 mg/ml gelatin.

Gel Filtration Chromatography—Receptor-ligand complex was formed by incubating 10 ml of $^{125}$I-labeled VEGF ($10^5$ cpm) with 100 ml of either wild-type or baculovirus sVEGF-RI-containing, infected Sf9 cell culture medium overnight at room temperature. The reaction products were separated on a Sephacryl S200 gel filtration column (0.7×25 cm) equilibrated in PBS, 1 mg/ml gelatin, at a flow rate of 15 ml/hr. Fractions (0.75 ml) were collected and analyzed in a g counter. Receptor-ligand complexes pass quickly through the column while the free labelled VEGF passes through more slowly. The results of this experiment shown in FIG. 4 demonstrate the formation of a high molecular weight complex between labelled VEGF and sVEGF-RI protein. This shows that sVEGF-RI binds VEGF.

Crosslinking—Purified sVEGF-RI (1–10 ng) was added to 25 ml of binding buffer (Dulbecco's Modified Eagle's medium (DME), 25 mM HEPES, pH 7.5, 0.3% gelatin), and $1 \times 10^5$ cpm of [$^{125}$I]-VEGF was added (FIG. 6, lane 1) with either 200 ng of unlabelled VEGF (lane 2) or bFGF (lane 3), then incubated 2 to 16 hours at room temperature. Bis (sulfosuccinimidyl)suberate (Pierce) crosslinker was added to a final concentration of 1 mM. The reaction was stopped after 15 min by the addition of boiling SDS PAGE sample buffer. The crosslinked products were separated by SDS PAGE on a 7.5% acrylamide gel and analyzed either by autoradiography or a phosphoimager. The results are shown in FIG. 6 and demonstrate that sVEGF-RI binds labelled VEGF by the appearance of two bands of about 145 kDa and 245 kDa. The 145 kDa band consists of one sVEGF-RI molecule and one VEGF molecule (Monomer, M.). The 245 kDa band apparently consists of two sVEGF-RI molecules and one VEGF dimer (D). Free VEGF ligand (L) dimers migrated at about 45 kDA.

Purified Ex-KDR and sFLT were each allowed to bind either [$^{125}$I]VEGF or [$^{125}$I]PlGF at 25° C. for 1 hr in a final volume of 25 µl in binding buffer (10 mM Hepes, pH 7.4, 0.01% BSA, 100 mM NaCl) with or without an excess of the appropriate unlabeled ligand. Competition binding was accomplished by incubation in the presence of various concentrations of unlabeled VEGF (0.1–400 nM). The reactions were then crosslinked with 1 mM BS$^3$ at 25° C. for 15 min followed by the addition of boiling Laemmli sample buffer (10). The crosslinked products were analyzed by SDS/7.5% PAGE and the complexes were visualized using a Phosphohnager (Molecular Dynamics, Sunnyvale, Calif.). In the competition crosslinking experiments the amount of radioactivity contained in the Ex-KDR/[$^{125}$I]VEGF complex as well as the uncomplexed [$^{125}$I]VEGF were quantified using the PhosphoImager.

Binding assay—The binding of sVEGF-RI to VEGF was analyzed using a 96 well plate assay as described by Duan, D-S. R. et al., supra. Briefly, sVEGF-RI, 50 to 200 ml partially purified by Mono Q chromatography (Pharmacia), was diluted to 10 ml in 25 mM TRIS, pH 7.4, 100 mM NaCl, 20 mM NH$_4$HCO$_3$. Aliquots (100 ml) were absorbed to the surface of a 96 well plate for 18 hours at 4° C., the plates were then washed twice with blocking buffer (DME, 25 mM HEPES, pH 7.5, 0.5% gelatin) and the nonspecific sites were blocked in the same buffer for 6 hours at 4° C. The plate was then washed twice in binding buffer. Various amounts of [$^{125}$I]VEGF were added to the wells in a final volume of 100 ml/well and incubated for 2 hours at room temperature. The wells were washed three times with 100 ml of binding buffer, the bound protein was solubilized with 100 ml of 1% SDS, 0.5% BSA and counted in a g counter. The results, shown in FIG. 7, were analyzed by the method of Scatchard [Scatchard, G., (1949) Ann. N.Y. Acad. Sci., 51, pp. 660–672]. The analysis demonstrates that sVEGF-RI retains high affinity binding for VEGF with a $K_d$ value of about 20 pM. This clearly demonstrates that sVEGF-RI, lacking the transmembrane region and adjacent Ig-like domain, binds VEGF with high affinity and that these regions are not required for VEGF binding.

Purified Ex-KDR and sFLT were each allowed to bind either [$^{125}$I]VEGF or [$^{125}$I]PlGF at 25° C. for 1 hour in a final volume of 25 µl in binding buffer (10 mM Hepes, pH 7.4, 0.01% BSA, 100 mM NaCl) with or without an excess of the appropriate unlabeled ligand. Competition binding was accomplished by incubation in the presence of various concentrations of unlabeled VEGF (0.1–400 nM). The reactions were then crosslinked with 1 mM BS$^3$ at 25° C. for 15 min followed by the addition of boiling Laemmli sample buffer. The crosslinked products were analyzed by SDS/7.5% PAGE and the complexes were visualized using a Phosphohnager (Molecular Dynamics, Sunnyvale, Calif.). In the competition crosslinking experiments the amount of radioactivity contained in the Ex-KDR/[$^{125}$I]VEGF complex as well as the uncomplexed [$^{125}$I]VEGF were quantified using the PhosphoImager.

To determine if sFLT and Ex-KDR bind VEGF and PlGF with high affinity, purified sFLT and Ex-KDR were each incubated with either [$^{125}$I]VEGF or [$^{125}$I]PlGF, covalently crosslinked and high molecular mass complexes were resolved by SDS/PAGE. sFLT formed high molecular mass complexes with both VEGF and PlGF whereas Ex-KDR formed complexes with VEGF but not with PlGF. The positions of the monomer (one VEGF dimer bound to one receptor molecule) and dimer (one VEGF dimer bound to two receptor molecules) were as expected. These radiolabeled complexes were competed by an excess of the same unlabeled VEGF or PlGF and thus are specific. PlGF was able to compete for VEGF binding to the sFLT receptor and VEGF competes for PlGF binding to this receptor. PlGF was not able to compete for [$^{125}$I]VEGF binding to Ex-KDR.

The affinity of VEGF for Ex-KDR was determined by a crosslinking competition binding assay since the Ex-KDR receptor binds poorly to 96 well plates. A constant amount of [$^{125}$I]VEGF was bound to Ex-KDR in the presence of increasing concentrations of unlabeled VEGF. The concentration of unlabeled VEGF required to displace 50% of the total [$^{125}$I]VEGF binding is approximately 1 nM, which is similar to the apparent $K_d$ for the membrane form of KDR.

Competition Between PlGF and VEGF for Binding to sFLT

Competitive binding of VEGF and PlGF to sFLT was analyzed by the 96 well plate binding assay. A constant amount of either [$^{125}$I]VEGF or [$^{125}$I]PlGF was bound to immobilized sFLT in the presence of increasing amounts of either unlabeled VEGF or PlGF. In comparison, 50% of the binding of [$^{125}$I]PlGF to sFLT was displaced by only 10 pM of VEGF. Approximately 110 pM of unlabeled PlGF displaced 50% of [$^{125}$I]PlGF binding to sFLT in agreement with saturation binding experiments. However, an approximately 5-fold higher concentration of PlGF (~550 pM) was required to displace 50% of the [$^{125}$I]VEGF binding to sFLT. These data indicate that VEGF and PlGF compete for the same site on sFLT at which VEGF binds with ~4-fold higher affinity than PlGF. Crosslinking competition experiments with sFLT gave similar results.

Here we show that VEGF binds to the extracellular domains of both FLT and KDR with high affinity. PlGF, however, only binds to the extracellular domain of FLT with high affinity and does not bind to the equivalent extracellular region of KDR. VEGF is able to compete efficiently for PlGF binding to sFLT whereas PlGF competes less efficiently for VEGF binding. These binding data demonstrate that VEGF complexes with sFLT somewhat tighter than does PlGF. Competitive binding infers that the VEGF and PlGF sites on sFLT are probably either overlapping or identical. Thus, sFLT will inhibit both PlGF and VEGF function.

EXAMPLE 4

Inhibition of VEGF binding by sVEGF-RI—The ability of sVEGF-RI to inhibit VEGF binding to HUVECs was tested.

HUVECs were plated at 50,000 cells/well in 24 well plates precoated with gelatin, and allowed to grow to confluence. A constant amount of [$^{125}$I]VEGF (100,000 cpm) was mixed with various amounts of partially purified sVEGF-RI in binding buffer, in a total volume of 200 μl and preincubated at room temperature for 1 hour. Samples were added to the cells and incubated for 4 hours at 4° C. with shaking. The medium was then aspirated and the cells were washed three times with binding buffer. The bound radioactivity was solubilized with 50 mM TRIS-HCl, pH 8.0, 150 mM NaCl, 1% NP40, 1% BSA and counted in a γ counter.

Figure 8:
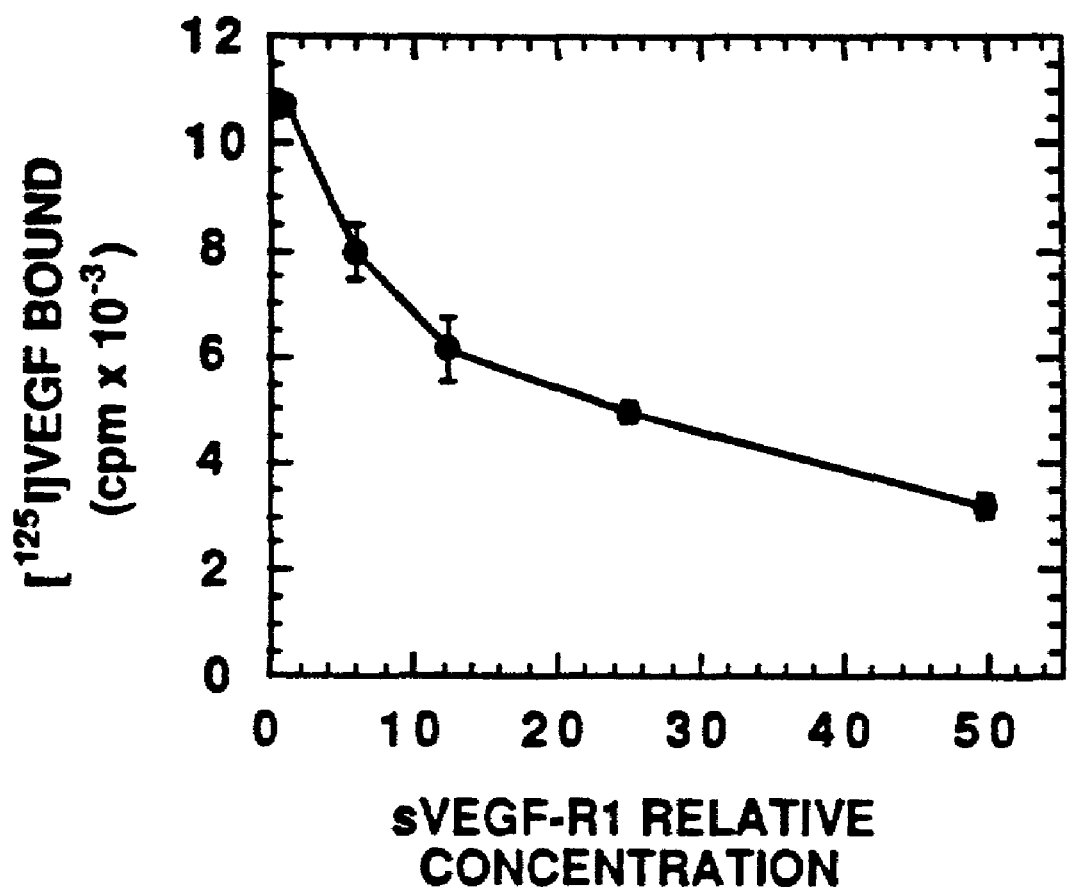
FIG. 8—Inhibition of [$^{125}$I]VEGF binding to HUVECs by sVEGF-RI is demonstrated.

The results are shown in FIG. 8. At the highest concentration of sVEGF-RI, VEGF binding to HUVECs was reduced by 70%. It may, however, be difficult to completely inhibit binding to the cellular membrane bound receptor since one molecule of sVEGF-R bound to a VEGF dimer may be able to bind to cell associated receptor to form an inactive (sVEGF-RI)-VEGF-(membrane spanning VEGF receptor) complex.

EXAMPLE 5

Inhibition of VEGF mediated mitogenesis by sVEGF-RI

Mitogenic inhibition—Since sVEGF-RI was able to inhibit VEGF binding to endothelial cells, it was then determined that the soluble receptor could inhibit VEGF induced mitogenesis in HUVECs. HUVECs were plated in gelatin coated 96 well plates at a density of 4000 cells/well in 100 ml of DME supplemented with 10% heat inactivated fetal calf serum plus antibiotics (penicillin G, 100 units/ml; streptomycin sulfate, 100 mg/ml). After 16 hours the medium was changed and test samples were added, cells were preincubated with a variable amount of purified sVEGF-RI for 15 minutes at 37° C. before growth factor (10 ng/ml) was added. The cells were incubated for 24 hours then [methyl-$^3$H]thymidine (0.8 mCi/well; 20 Ci/mmol:1 Ci=37 GBq, final specific activity of 0.8 mCi/nmole) was added followed by incubated for an additional 72 hours at 37° C. under 5% $CO_2$. The cells were then washed twice with Hank's balanced salt solution adjusted to pH 7.5 with 25 mM Hepes, 0.1% BSA. The cells were then lysed, the DNA was solubilized with 0.2 M $Na_2CO_3$, 0.1 M NaOH, and [$^3$H]thymidine incorporation was quantified by scintillation counting. The results are shown in FIG. 9. sVEGF-RI was able to completely inhibit VEGF induced [$^3$H]thymidine incorporation in HUVECs.

EXAMPLE 6

Purification of baculovirus expressed sVEGF-RI from Sf9 cells—Culture medium from Sf9 cells infected with a baculovirus construct designed to express sVEGF-RI (Example 2) was chromatographed through a heparin Sepharose CL-6B (Pharmacia) column (0.7×4 cm). The column was washed with 5 volumes of 10 mM Na-phosphate buffer, pH 6.2, 0.1 M NaCl, followed by 6 ml of 10 mM Na-phosphate buffer, pH 6.2, 0.6 M NaCl. The sVEGF-RI was eluted with 10 mM Na-phosphate buffer, pH 6.2, 1.0 M NaCl. Polyacrylamide gel electrophoresis was performed which demonstrated greater than 90% purity (as judged by coomassie blue staining) of the recombinantly produced sVEGF-R (FIG. 5). The identity of the protein was confirmed by N-terminal protein sequence analysis. The actual N-terminus (Ser Lys Leu . . . ) of the recombinant protein differs by two amino acids from that predicted by Shibuya et al., supra.

(Ser-Ser-Ser . . . ). The peptidase cleavage site in sVEGF-RI produced in Sf9 cells was between residues gly-26 and ser-27.

EXAMPLE 7

Figure 16:
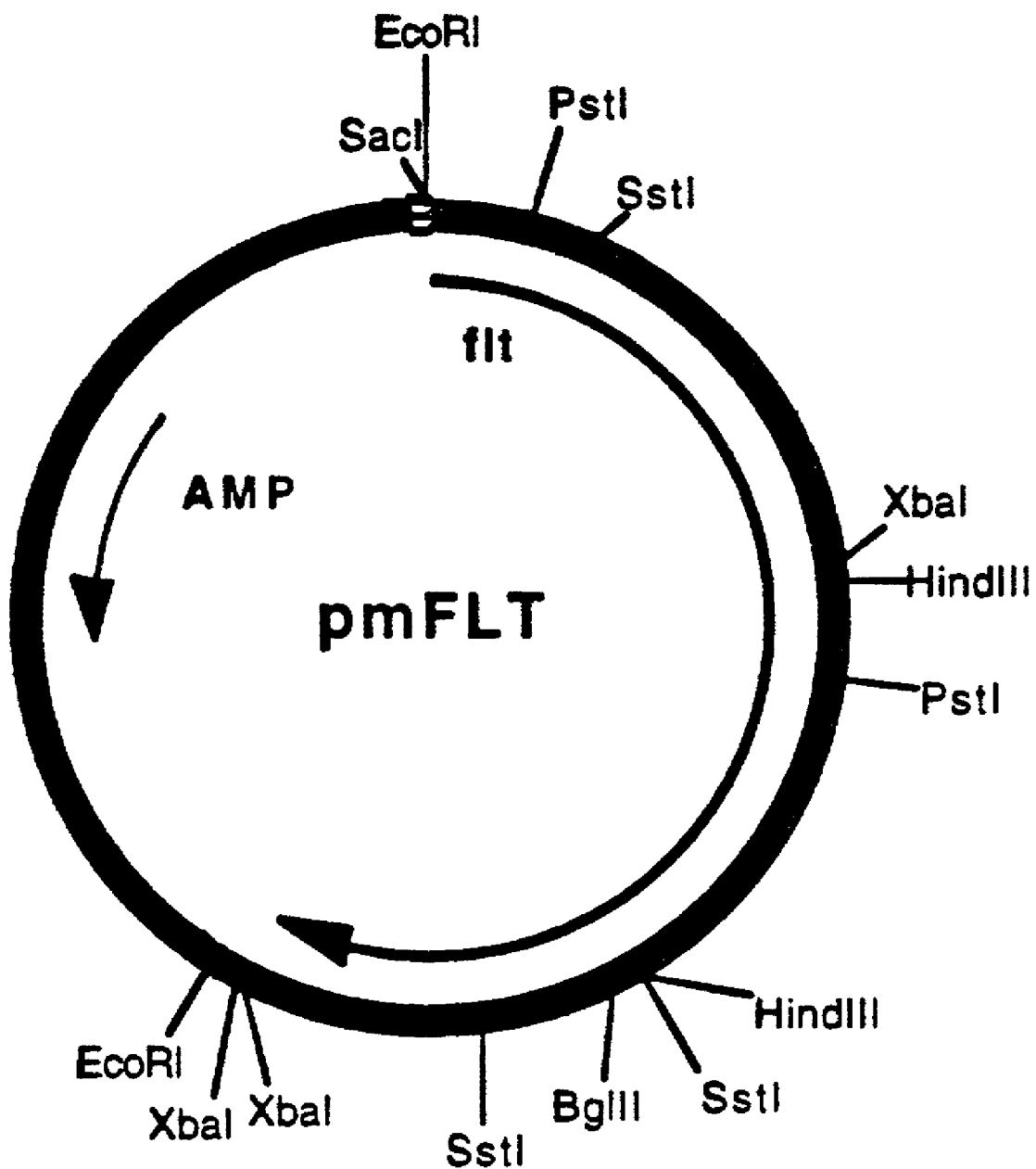
FIG. 16—A diagram of pmFLT is shown.
Figure 17:
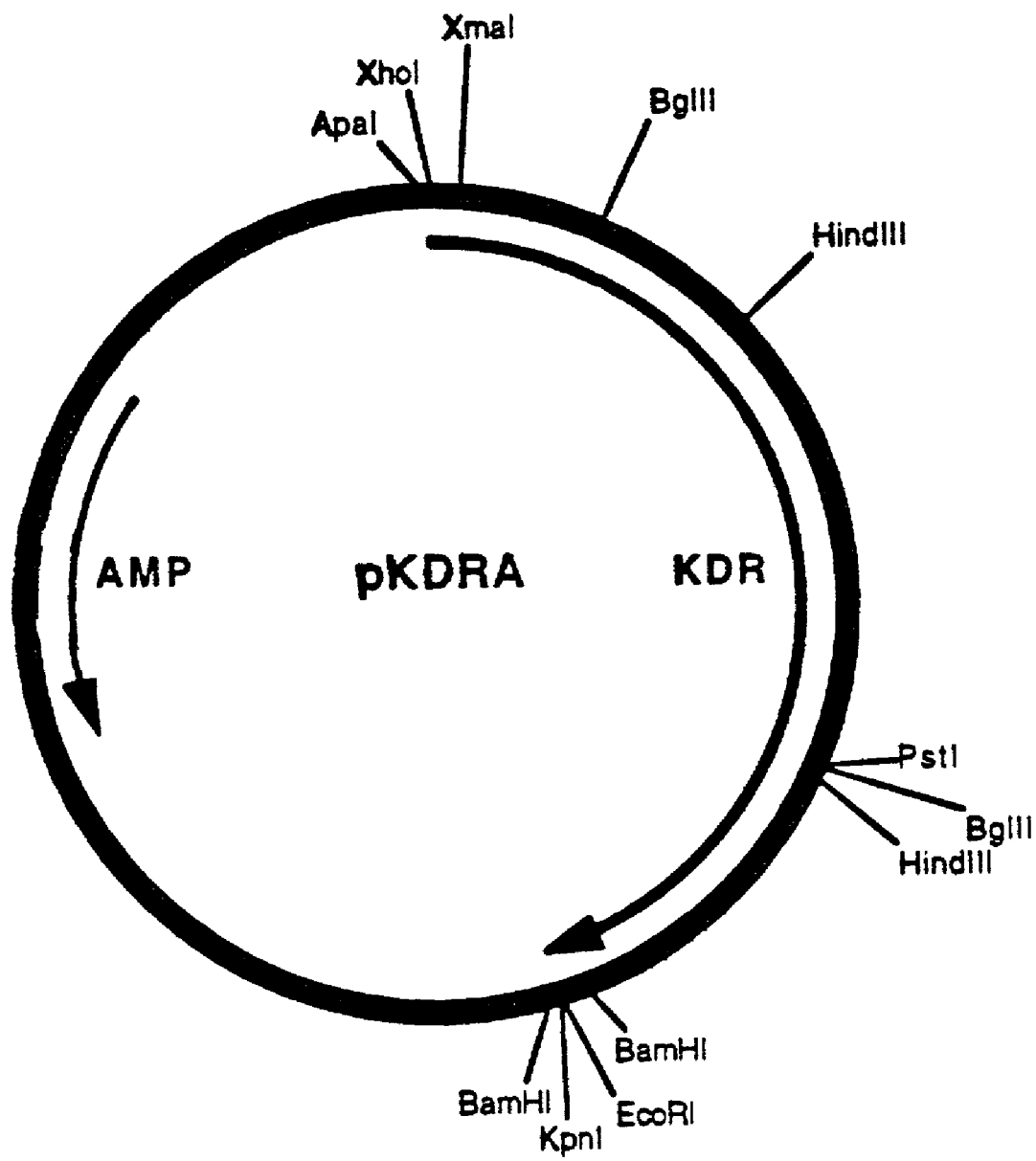
FIG. 17—A diagram of pKDRA is shown.

Construction of KDR-related sVEGF-R—Soluble forms of KDR (a known VEGF receptor) [Terman, B. I. et al., (1991) Oncogene 6, pp. 1677–1683; Terman, B. I. et al., (1992) Biochem. Biophys. Res. Comm. 187, pp. 1579–1586] may exist naturally but have not yet been identified. A soluble form of KDR is recombinantly constructed by modifying its coding sequence by PCR using the primers 1) 5' TTTTG-GATCCCTGCAGACAGATCTACGTTTGAGAACC 3' (SEQ. ID. NO.: 7) and 2) 5' TTTTGGATCCT-TAACGCTCTAGGACTGTGAGC 3' (SEQ. ID. NO.: 8), and pKDRA (the XhoI/EcoRI fragment coding for the extracellular and transmembrane domain of KDR cloned into the EcoRI site of pGEM 7Z obtained from Promega) as a template (FIG. 17). This generated a translation stop codon after amino acid residue number 663 of KDR which corresponds to the extracellular domain of full length KDR. This modified fragment is then used to replace the PstI/BamHI fragment of pKDRA generating a truncated form of the KDR gene (FIG. 10) which codes for a soluble receptor denoted sVEGF-RII (FIG. 11). The XhoI site at base pair number 257 is then changed to a BamHI site by standard cloning techniques. Another truncated form of the KDR receptor is created with primer 1 shown above, and primer 3) 5' TTTTGGATCCAACGGTCCCTAGGATGATGAC 3', (SEQ. ID. NO.: 9) (FIG. 12). This form of KDR, denoted VEGF-RTMII, is truncated at the C-terminal side of the transmembrane domain and therefore retains the transmembrane region (FIG. 13). A similar form of the FLT receptor is generated by PCR using the primers 4) 5' AGCACCT-TGGTTGTGGCTGACTC 3' (SEQ. ID. NO.: 10) and 5) 5' TTTTGGATCCTTAGATAAGGAGGGTTAATAGG 3' (SEQ. ID. NO.: 11) and plasmid pmFLT (full length flt cloned into the EcoRI site of pGEM3Z obtained from Promega) as a template (FIG. 16). The 780 base pair PCR fragment can then be cloned together with the EcoRI/XbaI fragment from pmFLT to produce an EcoRI/BAMHI fragment (FIG. 14) encoding a truncated form of FLT (denoted sVEGF-RTMI) which retains the transmembrane domain but lacks the cytoplasmic domain (FIG. 15). The EcoRI site at the 5' end of the gene is then modified to a BamHI site. The resulting truncated forms of KDR and FLT are then cloned into pBluebacIII (Stratagene) for expression in Sf9 insect cells. Characterization of these constructed truncated forms of VEGF receptors is accomplished by the techniques used to characterize sVEGF-RI as in Examples 2, 3, 4, 5, and 6.

EXAMPLE 8

Identification and Partial Purification of a Soluble VEGF Binding Protein

A mRNA encoding a soluble version of Flt was expressed in HUVECs. The recombinant sFlt protein, when expressed in Sf9 insect cells (BVsFlt), was found to bind tightly to heparin Sepharose. To determine if sFlt protein was expressed by HUVECs, conditioned medium from cultured HUVECs was filtered through a 0.22 μm membrane and passed over a heparin sepharose column. The heparin column was eluted with a step gradient and fractions were tested for binding to [$^{125}$I] VEGF by covalent crosslinking.

VEGF binding activity eluted at similar NaCl concentrations as the BVsFlt protein and was found in the 0.6–1.2 M NaCl step fraction. An equal volume of EndoUV medium (endothelial cell growth medium) not conditioned was chromatographed and had no VEGF binding activity in the 0.6–1.2 M NaCl fraction. The VEGF binding activity from HUVECs when crosslinked to labeled VEGF formed complexes which migrate slower on SDS/PAGE than VEGF complexes formed with BVsFlt. VEGF binding fractions were pooled and further separated by cation exchange chromatography with a linear NaCl gradient. Again, VEGF binding activity from the endothelial cell conditioned medium elutes at a similar position as BVsFlt.

The chromatography data shows that the partially purified HUVEC VEGF binding protein behaves similar to BVsFlt. To determine if this VEGF binding protein is related to Flt, antibodies against peptides based on the N-terminus and third immunoglobulin-like domain in the extracellular region of Flt were prepared. Fractions from the mono S column that produced high molecular weight complexes when covalently crosslinked to [$^{125}$I] VEGF were analyzed by Western blot analysis. These data show that a 116 kDa protein band which co-elutes with VEGF binding activity was detected by both antibodies, thus the binding activity isolated from human endothelial cells is a soluble form of Flt.

What is claimed is:

1. A method for inhibiting angiogenesis comprising the administration of a VEGF inhibitor protein in isolated form which comprises the amino acid sequence as set forth in SEQ ID NO:6.

2. A method for inhibiting angiogenesis comprising the administration of a VEGE inhibitor protein in isolated form which consists of the amino acid sequence as set forth in SEQ ID NO:6.

3. The method of claim 1 which further comprises administration of said VEGF inhibitor with a pharmaceutically acceptable carrier.

4. The method of claim 2 which further comprises administration of said VEGF inhibitor with a pharmaceutically acceptable carrier.

* * * * *